United States Patent
Hayano et al.

(10) Patent No.: US 7,131,949 B2
(45) Date of Patent: Nov. 7, 2006

(54) METHOD AND APPARATUS FOR EXAMINING VASCULAR ENDOTHELIAL FUNCTIONS

(75) Inventors: Junichiro Hayano, Nagoya (JP); Toshihiko Ogura, Komaki (JP)

(73) Assignee: Omron Healthcare Co., Ltd., Kyoto (JP)

( * ) Notice: Subject to any disclaimer, the term of this patent is extended or adjusted under 35 U.S.C. 154(b) by 295 days.

(21) Appl. No.: 10/822,843

(22) Filed: Apr. 13, 2004

(65) Prior Publication Data

US 2005/0228303 A1 Oct. 13, 2005

(51) Int. Cl.
*A61B 5/00* (2006.01)
(52) U.S. Cl. .................................. 600/500; 600/481
(58) Field of Classification Search .................. None
See application file for complete search history.

(56) References Cited

U.S. PATENT DOCUMENTS 6,440,079 B1 * 8/2002 Ogura et al. ................. 600/492

OTHER PUBLICATIONS

"Pulse Wave Velocity", First edition compiled by Toshio Ozawa and Yoshiaki Masuda; Published by Medical Review Co., Ltd. May 1, 2002; pp. 104-106.

* cited by examiner

Primary Examiner—Robert L. Nasser
Assistant Examiner—Karen Toth
(74) Attorney, Agent, or Firm—Oliff & Berridge, PLC

(57) ABSTRACT

Vascular endothelial function in terms of flow-mediated dilation (FMD) of peripheral arteries can be assessed reliably by measuring beat-to-beat pulse-wave conduction time (PCT) simultaneously for two symmetric segments of arteries locating on the right and left sides of body. When reactive hyperemia is induced in the peripheral tissues on one side, the time dependent changes in PCT caused by FMD on that side can be detected as the beat-to-beat differences in PCT between two sides (ΔPCT). ΔPCT would provide a sensitive and specific assessment of the FMD response, because the influences of the systemic changes in hemodynamic and neurohumoral factors common to both sides are subtracted out. In addition, measurement of PCT requires no skillful technique and is advantageous in that the apparatus is inexpensive.

5 Claims, 17 Drawing Sheets

METHOD AND APPARATUS FOR EXAMINING VASCULAR ENDOTHELIAL FUNCTIONS

BACKGROUND OF THE INVENTION

1. Field of the Invention

This invention relates to a method and apparatus for assessing vascular endothelial function.

2. Description of the Related Art

Vascular endothelium is a cell group that constitute a layer of lining blood vessels, functioning not only to line the inner wall of blood vessels and separate blood components from body tissues but also to produce or release substances which control the biological characteristics of blood vessels including dimension, elasticity, permeability and reactivity. Since impairment of vascular endothelial function is found in earlier stages of arteriosclerosis where arteriosclerosis has not yet developed or clinically manifested, it is possible to prevent the development or treat the arteriosclerosis earlier by detecting the impairment of vascular endothelial function.

A non-invasive method for assessing flow-mediated dilation induced by reactive hyperemia by using an ultrasonic device is known as a method for assessing vascular endothelial function (for example, as shown in the non-patent literature 1). The above reactive hyperemia is a transient increase in organ blood flow that takes place following a brief period of ischemia (arterial occlusion) and subsequent release. The flow-mediated dilation is a reaction in which an increased arterial blood flow stimulates vascular endothelium of the artery concerned, thus secreting from vascular endothelium endothelium-derived relaxing factors (EDRF; nitrogen monoxide and analogous substances), which are substances to dilate blood vessels, resulting in an increase in the diameter of the artery concerned. As a result, since endothelium-derived relaxing factors are secreted at a smaller quantity when the vascular endothelial function is impaired, the diameter of the artery will not increase as expected even after an increase in arterial blood flow caused by the reactive hyperemia. Thus, vascular endothelial function can be assessed by referring to the extent of the increase in diameter of the artery with the peripheral reactive hyperemia.

In the method described in the non-patent literature 1, an ultrasonic probe was used to provide consecutive images of an artery by which a maximum increase rate of the arterial diameter after release from ischemia in relation to that before the ischemia was calculated to assess vascular endothelial function based on the maximum increase rate. The above maximum increase rate is called % FMD (flow mediated dilatation), which is about 10% for healthy adults. 3 to 4% FMD is indicative of endothelial dysfunction and likely that arteries in major organs have already been atherosclerotic or may have an increased risk for arteriosclerosis.

Methods for inducing release of endothelium-derived relaxing factors from vascular endothelium include methods for causing the above hyperemic reaction or increased blood flow and for injecting into an artery substances stimulating the release of EDRF such as acetylcholine.

[Non-patent Literature 1]

Page 104 to 106, "Pulse Wave Velocity," First edition compiled by Toshio Ozawa and Yoshiaki Masuda, Published by Medical Review Co., Ltd. May 1, 2002

However, the following problems are found in the method for calculating % FMD by referring to the vasodilation response assessed by an ultrasonic device. First, a major problem with the method is the large variation in results, as high as 2 to 3%, among examiners and laboratories. Since the % FMD is considered normal at about 10% and abnormal at 3 to 4%, a variation of as high as 2 to 3% poses a serious problem. The great variation is due to the need for skill in detecting correct signals such as placing an ultrasonic probe vertically to a vessel, and variation in the point of time in determining a diameter of the vessel because it is necessary to detect from consecutive images of a pulsating blood vessel the timing when the greatest dilation of the vessel takes place after release from ischemia, and also to determine a diameter of the blood vessel at the end of diastolic phase of the heart. Therefore, it may take several months to acquire this skill, and it is reported that % FMD is not reliable unless the result is obtained from an examiner with substantial experience (for example, about six-months). Second, this method has an inevitable theoretical limitation. The arterial diameter shows not only pulsation but also spontaneous variations. The arterial diameter is dependent on heart rate and blood pressure, both of which show, even in a short term, physiological fluctuation such as those relating respiration and Mayer wave (10-second rhythm). Also, neurohumoral, thermoregulatory and emotional factors (which could accompany arterial occlusion) affect the vascular tone directly and indirectly through heart rate and blood pressure. The influences of these systemic factors confound the assessment of endothelium-dependent vascular responses and partly contribute to the large variation of % FMD. Finally, in case of the brachial artery, the diameter of blood vessel is about 5 mm and expected change of the diameter would be less than 0.5 mm, or dilation corresponding to less than 10% of a diameter of the vessel. Thus, such exact detection requires a high-performance and highly priced ultrasonic device, which is another problem.

SUMMARY OF THE INVENTION

This invention has been made in view of these problems, with the objective of providing a method and apparatus for assessing vascular endothelial function, which realize a highly reliable assessment of vascular endothelial function with excluding the influences of the systemic factors, do not require a great amount of skill, and is low in cost.

The above object may be achieved according to a first aspect of this invention, which provides a method for assessing vascular endothelial function, comprising; (a) a stimulation step of giving stimulation for inducing a release of endothelium-derived relaxing factors from vascular endothelium to a specified region of the artery in a living body, (b) a pre-stimulation measurement step of measuring, before said stimulation step, almost simultaneously first pulse-wave-conduction-velocity-relating information which is a pulse-wave-conduction-velocity-relating information related to the velocity at which a pulse conducts through the first segment including a part or a whole of the specified region of the artery and second pulse-wave-conduction-velocity-relating information which is said pulse-wave-conduction-velocity-relating information of the artery in the second segment almost symmetric to said first segment with respect to the median plane, (c) a post-stimulation measurement step of measuring said first pulse-wave-conduction-velocity-relating information and said second pulse-wave-conduction-velocity-relating information after said stimulation step, and (d) a comparative value calculation step of calculating respectively the pre-stimulation comparative value representing a difference or ratio of the first pulse-wave-conduction-velocity-relating information to the second pulse-wave-conduction-velocity-relating information obtained at said pre-stimulation measurement step and the post-stimulation comparative value representing a difference or ratio of the first pulse-wave-conduction-velocity-relating information to the second pulse-wave-conduction-velocity-relating information obtained at said post-stimulation measurement step.

In the first preferred form of the method according to the first aspect of the invention, said first segment is a segment from the heart to a specified point on said artery and said second segment is a segment almost symmetric to a segment from the heart to a specified point on said artery with respect to the median plane.

In the second preferred form of the method according to the first aspect of the invention, (a) in said pre-stimulation measurement step, an almost simultaneous measurement is carried out for third pulse-wave-conduction-velocity-relating information which is said pulse-wave-conduction-velocity-relating information at the predetermined third segment closer to the central side rather than said first segment with regard to said artery and also for fourth pulse-wave-conduction-velocity-relating information which is said pulse-wave-conduction-velocity-relating information at a fourth segment almost symmetric to said third segment with respect to the median plane, in addition to the first pulse-wave-conduction-velocity-relating information and the second pulse-wave-conduction-velocity-relating information, (b) in said post-stimulation measurement step, an almost simultaneous measurement is carried out for the third pulse-wave-conduction-velocity-relating information and the fourth pulse-wave-conduction-velocity-relating information, in addition to the first pulse-wave-conduction-velocity-relating information and the second pulse-wave-conduction-velocity-relating information, and (c) in said comparative value calculation step, respective calculations are carried out for the pre-stimulation comparative value on the central side representing a difference or ratio of the third pulse-wave-conduction-velocity-relating information to the fourth pulse-wave-conduction-velocity-relating information obtained at said pre-stimulation measurement step and also for the post-stimulation comparative value on the central side representing a difference or ratio of the third pulse-wave-conduction-velocity-relating information to the fourth pulse-wave-conduction-velocity-relating information obtained at said post-stimulation measurement step, in addition to the pre-stimulation comparative value on the peripheral side representing a difference or ratio of the first pulse-wave-conduction-velocity-relating information to the second pulse-wave-conduction-velocity-relating information obtained at said pre-stimulation measurement step and the post-stimulation comparative value on the peripheral side representing a difference or ratio of the first pulse-wave-conduction-velocity-relating information to the second pulse-wave-conduction-velocity-relating information obtained at said post-stimulation measurement step.

In the third preferred form of the method according to the first aspect of the invention, said comparative value calculation step is a step of calculating successively said post-stimulation comparative values, and further comprising vascular endothelial dysfunction judgment step for judging the presence and extent of vascular endothelial dysfunction on the basis of the fact that an absolute value of a difference between a peak value of the post-stimulation comparative value and the pre-stimulation comparative value calculated successively by the comparative value calculation step is at or lower than a predetermined judgment standard value.

The object may also be achieved according to a second aspect of the present invention, which provides a method for assessing vascular endothelial function, comprising; (a) a stimulation step of giving stimulation for inhibiting the release of endothelium-derived relaxing factors from vascular endothelium and also for inhibiting vascular dilation resulting from the release of said endothelium-derived relaxing factors to a specified region of the artery in a living body, (b) a pre-stimulation measurement step of measuring, before said stimulation step, almost simultaneously first pulse-wave-conduction-velocity-relating information which is pulse-wave-conduction-velocity-relating information related to the velocity at which a pulse conducts through the first segment including a part or a whole of the specified region of the artery and second pulse-wave-conduction-velocity-relating information which is said pulse-wave-conduction-velocity-relating information of the artery in the second segment almost symmetric to said first segment with respect to the median plane, (c) a post-stimulation measurement step of measuring said first pulse-wave-conduction-velocity-relating information and said second pulse-wave-conduction-velocity-relating information after said stimulation step, and (d) a comparative value calculation step of calculating respectively the pre-stimulation comparative value representing a difference or ratio of the first pulse-wave-conduction-velocity-relating information to the second pulse-wave-conduction-velocity-relating information obtained at said pre-stimulation measurement step and the post-stimulation comparative value representing a difference or ratio of the first pulse-wave-conduction-velocity-relating information to the second pulse-wave-conduction-velocity-relating information obtained at said post-stimulation measurement step.

In the first preferred form of the method according to the second aspect of the invention, said first segment is a segment from the heart to a specified point on said artery and said second segment is a segment almost symmetric to a segment from the heart to a specified point on said artery with respect to the median plane.

In the second preferred form of the method according to the second aspect of the invention, (a) in said pre-stimulation measurement step, an almost simultaneous measurement is carried out for third pulse-wave-conduction-velocity-relating information which is said pulse-wave-conduction-velocity-relating information at the predetermined third segment closer to the central side rather than said first segment with regard to said artery and also for fourth pulse-wave-conduction-velocity-relating information which is said pulse-wave-conduction-velocity-relating information at a fourth segment almost symmetric to said third segment with respect to the median plane, in addition to the first pulse-wave-conduction-velocity-relating information and the second pulse-wave-conduction-velocity-relating information, (b) in said post-stimulation measurement step, an almost simultaneous measurement is carried out for the third pulse-wave-conduction-velocity-relating information and the fourth pulse-wave-conduction-velocity-relating information, in addition to the first pulse-wave-conduction-velocity-relating information and the second pulse-wave-conduction-velocity-relating information, and (c) in said comparative value calculation step, respective calculations are carried out for the pre-stimulation comparative value on the central side representing a difference or ratio of the third pulse-wave-conduction-velocity-relating information to the fourth pulse-wave-conduction-velocity-relating information obtained at said pre-stimulation measurement step and also for the post-stimulation comparative value on the central side representing a difference or ratio of the third pulse-wave-conduction-velocity-relating information to the fourth pulse-wave-conduction-velocity-relating information obtained at said post-stimulation measurement step, in addition to the pre-stimulation comparative value on the peripheral side representing a difference or ratio of the first pulse-wave-conduction-velocity-relating information to the second pulse-wave-conduction-velocity-relating information obtained at said pre-stimulation measurement step and the post-stimulation comparative value on the peripheral side representing a difference or ratio of the first pulse-wave-conduction-velocity-relating information to the second pulse-wave-conduction-velocity-relating information obtained at said post-stimulation measurement step.

In the third preferred form of the method according to the second aspect of the invention, said comparative value calculation step is a step of calculating successively said post-stimulation comparative values, and further comprising vascular endothelial dysfunction judgment step for judging the presence and extent of vascular endothelial dysfunction on the basis of the fact that an absolute value of a difference between a peak value of the post-stimulation comparative value and the pre-stimulation comparative value calculated successively by the comparative value calculation step is at or lower than a predetermined judgment standard value.

The object may also be achieved according to a third aspect of the present invention, which provides an apparatus for assessing vascular endothelial function, comprising; (a) an arterial occlusion apparatus for occluding arteries to cause ischemia of a specified region of tissue in a living body for more than a predetermined time, (b) a pulse-wave-conduction-velocity-relating information measurement apparatus for measuring successively said first pulse-wave-conduction-velocity-relating information which is a pulse-wave-conduction-velocity-relating information related to the velocity at which a pulse conducts through the artery in the first segment including a part or a whole of the specified region of said artery and the second pulse-wave-conduction-velocity-relating information which is said pulse-wave-conduction-velocity-relating information of the artery in the second segment almost symmetric to said first segment with respect to the median plane, and (c) comparative value calculating means for calculating the pre-ischemic comparative value representing a difference or ratio of said first pulse-wave-conduction-velocity-relating information to said second pulse-wave-conduction-velocity-relating information before ischemia (arterial occlusion) by said arterial occlusion apparatus and also for calculating the post-ischemic comparative value representing a difference or ratio of said first pulse-wave-conduction-velocity-relating information to said second pulse-wave-conduction-velocity-relating information after release from ischemia (arterial occlusion) by said arterial occlusion apparatus.

In the first preferred form of the apparatus according to the third aspect of the invention, said first segment is a segment from the heart to a specified point on said artery and said second segment is a segment almost symmetric to a segment from the heart to a specified point on said artery with respect to the median plane.

In the second preferred form of the apparatus according to the third aspect of the invention, said comparative value calculating means is for calculating successively said post-ischemic comparative value, and further comprising vascular endothelial dysfunction judgment means for judging the presence and extent of vascular endothelial dysfunction on the basis of the fact that an absolute value of a difference between a peak value of the post-ischemic comparative value and the pre-ischemic comparative value calculated successively by the comparative value calculating means is at or lower than a predetermined judgment standard value.

In the third preferred form of the apparatus according to the third aspect of the invention, said comparative value calculating means is for calculating successively said post-ischemic comparative value, and further comprising an output apparatus for illustrating graphically changes over time in comparative values calculated successively by said comparative value calculating means.

In the fourth preferred form of the apparatus according to the third aspect of the invention, (a) said first segment is closer to the peripheral side than a region of arterial occlusion by said arterial occlusion apparatus, (b) said pulse-wave-conduction-velocity-relating information measurement apparatus is for measuring almost simultaneously the third pulse-wave-conduction-velocity-relating information which is said pulse-wave-conduction-velocity-relating information at the specified third segment closer to the central side rather than said region of arterial occlusion and the fourth pulse-wave-conduction-velocity-relating information which is said pulse-wave-conduction-velocity-relating information at the fourth segment almost symmetric to said third segment with respect to the median plane, in addition to said first pulse-wave-conduction-velocity-relating information and the second pulse-wave-conduction-velocity-relating information, and (c) said comparative value calculating means is for calculating respectively the pre-ischemic comparative value on the central side representing a difference or ratio of said third pulse-wave-conduction-velocity-relating information to said fourth pulse-wave-conduction-velocity-relating information obtained before ischemia by said arterial occlusion apparatus and post-ischemic comparative value on the central side representing a difference or ratio of the third pulse-wave-conduction-velocity-relating information to the fourth pulse-wave-conduction-velocity-relating information obtained after release from ischemia (arterial occlusion) by said arterial occlusion apparatus, in addition to the pre-ischemic comparative value on the peripheral side representing a difference or ratio of said first pulse-wave-conduction-velocity-relating information to the second pulse-wave-conduction-velocity-relating information obtained before ischemia by said arterial occlusion apparatus and post-ischemic comparative value on the peripheral side representing a difference or ratio of said first pulse-wave-conduction-velocity-relating information to said second pulse-wave-conduction-velocity-relating information obtained after release from ischemia (arterial occlusion) by said arterial occlusion apparatus.

According to the first aspect of the present invention, since the first pulse-wave-conduction-velocity-relating information to be measured at the post-stimulation measurement step is affected by dilation of the vessels and reduced elasticity of the vessel walls due to the release of endothelium-derived relaxing factors from vascular endothelium in the stimulation step, it varies depending on the first pulse-wave-conduction-velocity-relating information to be measured at the pre-stimulation measurement step. The first pulse-wave-conduction-velocity-relating information by itself shows spontaneous variations due to the influence of systemic fluctuations in blood pressure, heart rate and other factors, which obscure the changes after the stimulations. However, in the first invention, the second pulse-wave-conduction-velocity-relating information is also measured.

Since this second pulse-wave-conduction-velocity-relating information is pulse-wave-conduction-velocity-relating information at the second segment almost symmetric to the first segment with respect to the median plane, it is approximately similar to the first pulse-wave-conduction-velocity-relating information in the spontaneous variations. A comparative value to be calculated at the comparative value calculation step is a difference or ratio of the first pulse-wave-conduction-velocity-relating information to the second pulse-wave-conduction-velocity-relating information. Therefore, the comparative value is not affected by the influence of the systemic fluctuations in blood pressure, heart rate and other factors. Since comparison of the pre-stimulation comparative value and the post-stimulation comparative value would make clear the change in stimulation-derived first pulse-wave-conduction-velocity-relating information, vascular endothelial function can be assessed at a high reliability by referring to the assessment of vascular endothelial function on the basis of comparison of the pre-stimulation comparative value with the post-stimulation comparative value. In addition, measurement of the pulse-wave-conduction-velocity-relating information does not require a great amount of skill and is also advantageous in that an apparatus is inexpensive.

In the first aspect of the present invention, stimulation is given for inducing the release of endothelium-derived relaxing factors from vascular endothelium during the stimulation step, whereas in the second aspect of the present invention, stimulation is given to a living body for inhibiting the release of endothelium-derived relaxing factors from the vascular endothelium and also for inhibiting vascular dilation due to the release of endothelium-derived relaxing factors. This is the only difference between them, with the same effect obtained also from the second aspect of the present invention.

The first preferred forms of the first, second and third aspects of the invention show specific modes of the first and the second segments. As shown herein, where one end of the first segment is the heart, the segment partially overlaps with the second segment. However, in executing the invention other than the first preferred forms of the first, second and third aspects of the invention, the first segment may or may not partially overlap with the second segment.

In the second forms of the first and second aspects of the invention, the pulse-wave-conduction-velocity-relating information at the first segment closer to the peripheral side rather than a local site where stimulation is given and the pulse-wave-conduction-velocity-relating information at the second segment, which constitutes a pair with the first segment, are referred to in the comparative value calculation step to calculate the comparative value before or after the stimulation closer to the peripheral side rather than the local site. In addition, the third and the fourth pulse-wave-conduction-velocity-relating information before and after the stimulation are calculated respectively at the third segment on the central side of an artery where the stimulation is given and at the fourth segment, which constitutes a pair with the third segment. The third and the fourth pulse-wave-conduction-velocity-relating information are referred to in the comparative value calculation step to calculate the comparative value on the central side before and after the stimulation. It is thus possible to separate vascular endothelial function of an artery to be stimulated into those on the peripheral side and those on the central side and evaluate them at the same time.

The third forms of the first and second aspects of the invention shows a specific embodiment for judging vascular endothelial function on the basis of the pre-stimulation comparative value and post-stimulation comparative value.

According to the third aspect of the invention, when the first pulse-wave-conduction-velocity-relating information measured by the apparatus for measuring pulse-wave-conduction-velocity-relating information after the release from ischemia (arterial occlusion) by the arterial occlusion apparatus is affected by dilation of the vessels and reduced elasticity of the vessel walls due to the flow-mediated dilation response after the release from ischemia, it undergoes changes in the first pulse-wave-conduction-velocity-relating information to be measured before ischemia. The first pulse-wave-conduction-velocity-relating information by itself shows spontaneous variations due to the influence of systemic fluctuations in blood pressure, heart rate and other factors, which obscure the changes after release from ischemia. However, in the third aspect of the invention where the second pulse-wave-conduction-velocity-relating information is measured, the second pulse-wave-conduction-velocity-relating information is the pulse-wave-conduction-velocity-relating information at the second segment almost symmetric to the first segment with respect to the median plane. Since the spontaneous variations are approximately similar to the first pulse-wave-conduction-velocity-relating information and a comparative value to be calculated at the comparative value calculating means is a difference or ratio of the first pulse-wave-conduction-velocity-relating information to the second pulse-wave-conduction-velocity-relating information, the comparative value is not affected by the spontaneous variations due to the influence of systemic fluctuations in blood pressure, heart rate and other factors. Therefore, since comparison of the pre-ischemic comparative value with the post-ischemic comparative value would make clear the changes caused by the reactive hyperemia in the first pulse-wave-conduction-velocity-relating information, vascular endothelial function can be assessed at high reliability by referring to the assessment of vascular endothelial function on the basis of comparison of the pre-ischemic comparative value and the post-ischemic comparative value. In addition, measurement of the pulse-wave-conduction-velocity-relating information does not require a great amount of skill and is advantageous in that the apparatus is inexpensive.

In the second form of the third aspect of the invention, the vascular endothelial dysfunction determination means is used to judge the presence and extent of vascular endothelial dysfunction by referring to a peak of the comparative value calculated after the release from ischemia (arterial occlusion) by the comparative value calculating means and also to a comparative value before ischemia, which is advantageous in making an automatic judgment of the vascular endothelial function.

In the third form of the third aspect of the invention, changes over time in post-ischemic comparative values are graphically given by an output apparatus, and a point in time when the blood vessel diameter dilates to the greatest extent after release from ischemia appears as a peak in a graph showing changes over time in the post-ischemic comparative values. Therefore, it is possible to determine easily a point in time when the blood vessel diameter undergoes the greatest dilation by referring to the graph.

In the fourth form of the third aspect of the invention, the pulse-wave-conduction-velocity-relating information at the first segment closer to the peripheral side rather than the arterial occlusion site and the pulse-wave-conduction-velocity-relating information at the second segment, which constitutes a pair with the first segment, are referred to in the comparative value calculating means to calculate the comparative value before or after the ischemia closer to the peripheral side rather than the arterial occlusion site. In addition, the third and the fourth pulse-wave-conduction-velocity-relating information before and after the ischemia are respectively calculated at the third segment on the central side of an artery to be occluded and at the fourth segment, which constitutes a pair with the third segment. The third and the fourth pulse-wave-conduction-velocity-relating information are referred to by the comparative value calculating means to calculate the comparative value on the central side before and after the ischemia. It is thus possible to separate vascular endothelial function of an artery to be occluded into those on the peripheral side and those on the central side and evaluate them at the same time.

BRIEF DESCRIPTION OF THE DRAWINGS

The above and other objects, features, advantages and technical and industrial significances of the present invention will be better understood by reading the following detailed description of presently preferred embodiment of the invention, when considered in connection with the accompanying drawings, in which.

DETAILED DESCRIPTION OF THE PREFERRED EMBODIMENT

Figure 1:
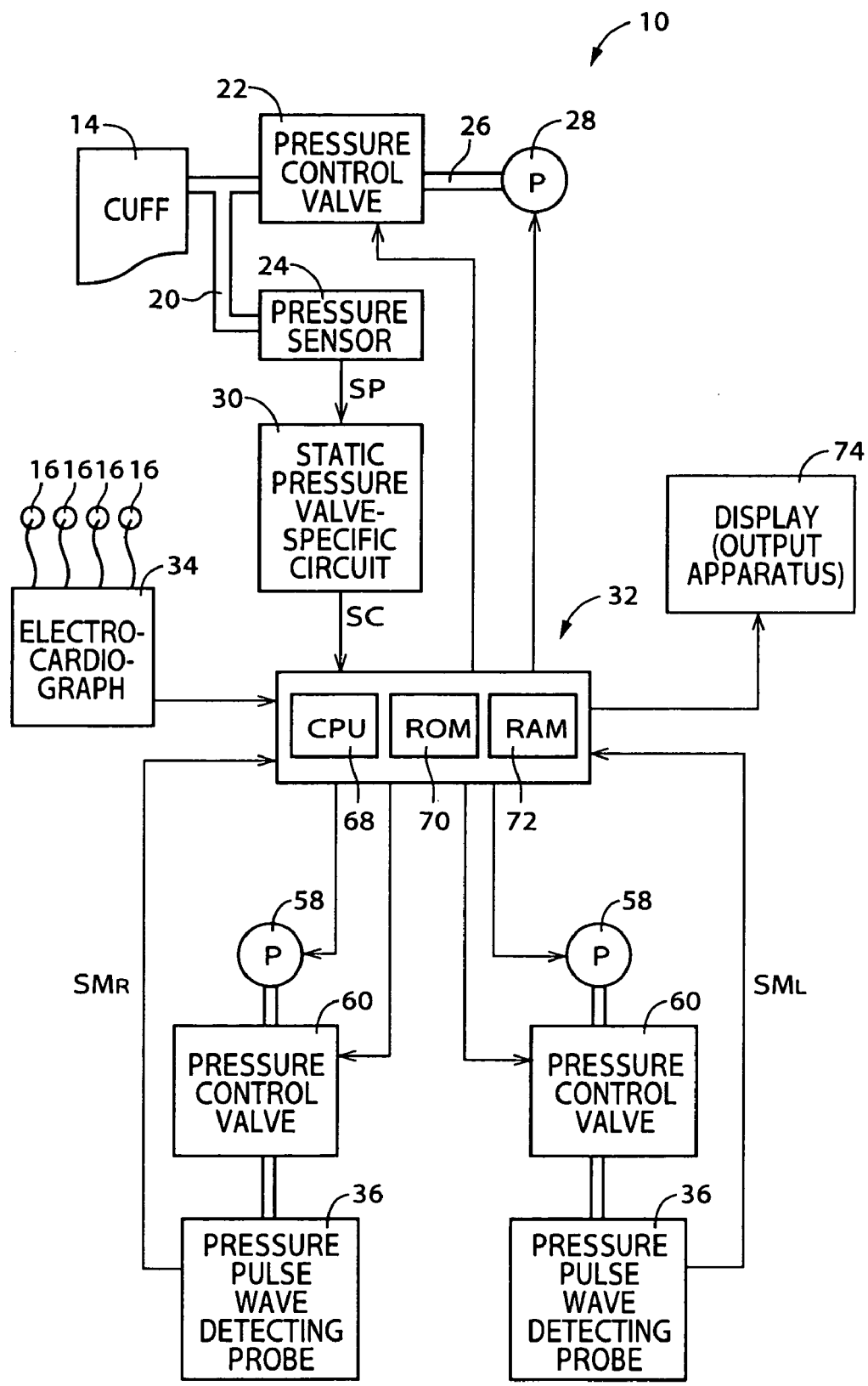
FIG. 1 is a block diagram explaining the structure of the vascular endothelial function assessment apparatus used in the present invention.
Figure 2:
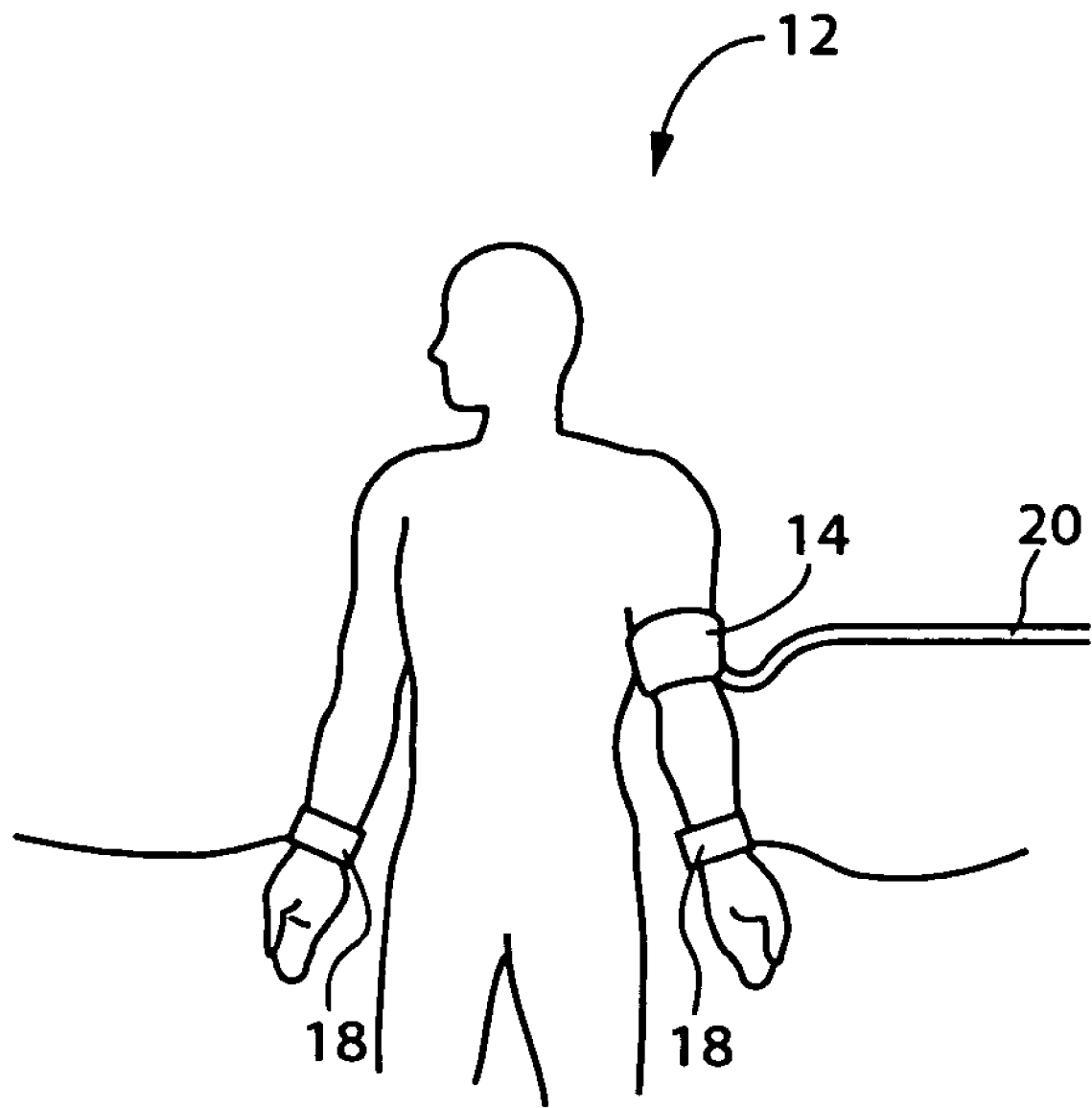
FIG. 2 is a view showing a state where the cuff and the pressure pulse wave detecting probe provided in the vascular endothelial function assessment apparatus of FIG. 1 are attached to the patient.

An embodiment of the present invention will be hereinafter described with reference to the drawings. FIG. 1 is a block diagram illustrating the structure of vascular endothelial function assessing apparatus 10 to which the invention is applied. FIG. 2 is a view showing a state where the a cuff 14 and a pressure pulse wave detecting probe 18 provided in the vascular endothelial function assessing apparatus 10 in FIG. 1 are attached to a patient 12.

As shown in FIG. 2, the cuff 14 is attached to an upper arm (the left upper arm in this instance) of the patient 12, and two pressure pulse wave detecting probes 18 are respectively attached to the left and right wrists of the patient 12.

As shown in FIG. 1, the cuff 14 is connected through a piping 20 to a pressure control valve 22 and a pressure sensor 24, and the pressure control valve 22 is further connected through a piping 26 to a pneumatic pump 28. The pressure control valve 22 controls a highly pressurized air produced by the pneumatic pump 28 to supply it into the cuff 14, or controls the pressure inside the cuff 14 by releasing air inside the cuff 14.

The pressure sensor 24 detects a pressure inside the cuff 14 to supply a pressure signal SP indicating the pressure to a static pressure valve-specific circuit 30. The static pressure valve-specific circuit 30 is provided with a low-pass filter and is able to discriminate a cuff pressure signal SC representing a stationary pressure contained in the pressure signal SP, that is, pressing pressure of the cuff 12 (hereinafter referred to as cuff pressure PC), thus supplying the cuff pressure signal SC through an A/D converter (not illustrated) to an electronic control device 32.

A plural number of electrodes 16 are attached at specified sites of the patient 12 to measure an electrocardiogram. No particular restriction is given to a method for introducing the electrocardiogram, and any method such as a bipolar limb lead and chest lead can be used. The above electrodes 16 are connected to an electrocardiograph 34, which amplifies an electrocardiographic signal SE introduced from the electrodes 16 and supplies it through the A/D converter (not illustrated) to the electronic control device 32. The above electrocardiographic signal SE represents an action potential of cardiac muscles, namely, an electrocardiogram.

Figure 3:
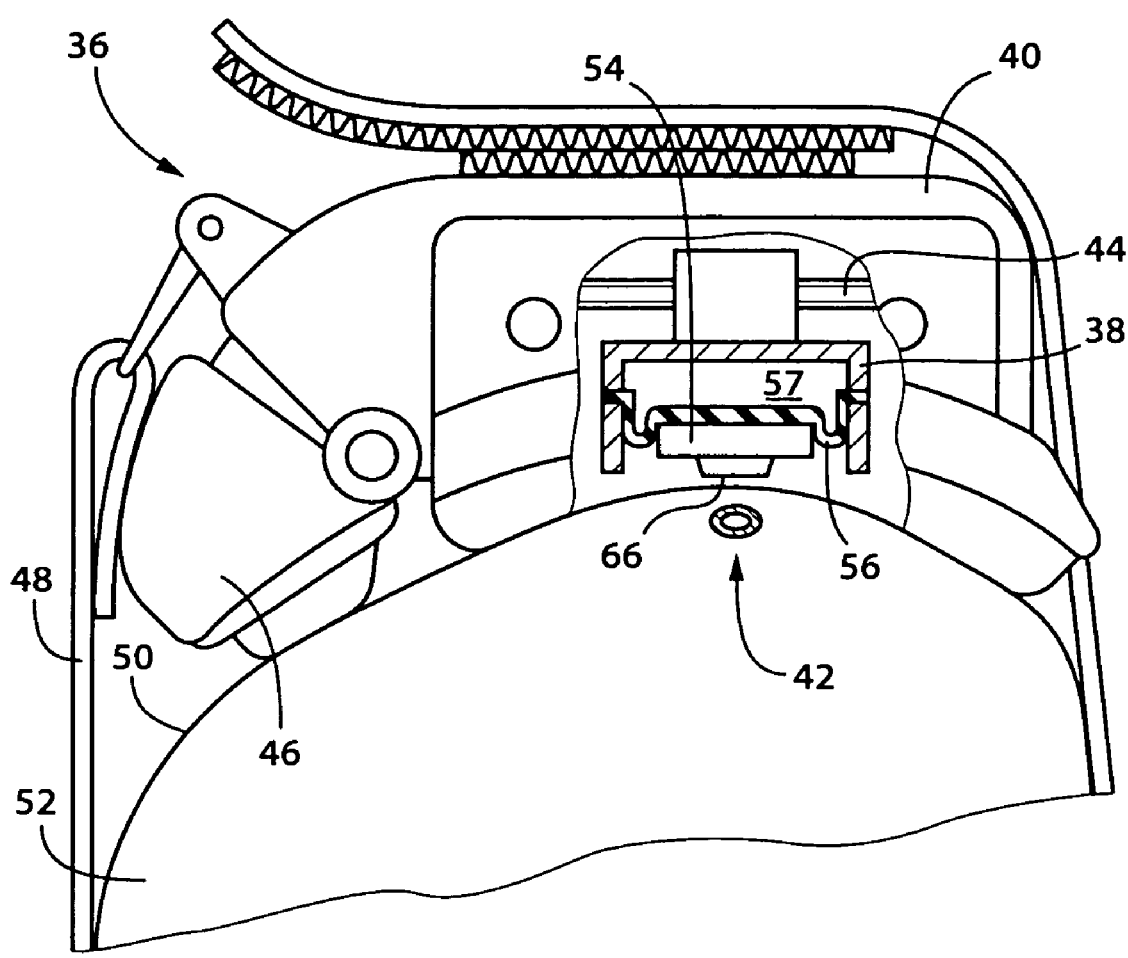
FIG. 3 is a view showing in detail the structure of the pulse wave detection probe of FIG. 1.

Two units of the pressure pulse wave detecting probes 18 are identical in structure. As displayed in detail in FIG. 3, these are provided with a container-like sensor housing 38, a case 40 accommodating the sensor housing 38, a screw axis 44 which is screwed down to the sensor housing 38 and is also able to move the sensor housing 38 toward a radial artery 42 through rotational driving, as well as a driving part 46 which is housed inside the case 40 and provided with a motor (not illustrated) for rotating and driving the screw axis 44. The above case 40 is also provided with an attachment band 48.

The thus structured pressure pulse wave detecting probe 18 is attached through the attachment band 48 to the wrist 52 in an easily attachable and detachable manner so that an open end of the sensor housing 38 is located opposite to the body surface 50.

A pressure pulse wave sensor 54 is provided inside the above sensor housing 38 through a diaphragm 56 in such a manner that it can be moved relatively toward the sensor housing 38 and also projected through an opening end of the sensor housing 38. A pressure chamber 57 is constituted with the sensor housing 38, diaphragm 56 and others. As shown in FIG. 1, the pressure chamber 57 is structured so as to receive highly pressurized air from the pneumatic pump 58 through the pressure control valve 60, by which the pressure pulse wave sensor 54 is pressed against the body surface 50 by HDP (hold down pressure) in accordance with the pressure inside the pressure chamber 57.

The above sensor housing 38 and the diaphragm 56 constitute a hold-down apparatus 62 for pressing the pressure pulse wave sensor 54 toward the radial artery 42. A motor made up of the screw axis 44 and the driving part 46 (not illustrated) constitutes a width-direction moving apparatus 64 for moving a hold-down pressure position at which the pressure pulse wave sensor 54 is pressed toward the body surface 50 in the width direction of the radial artery 42.

Figure 4:
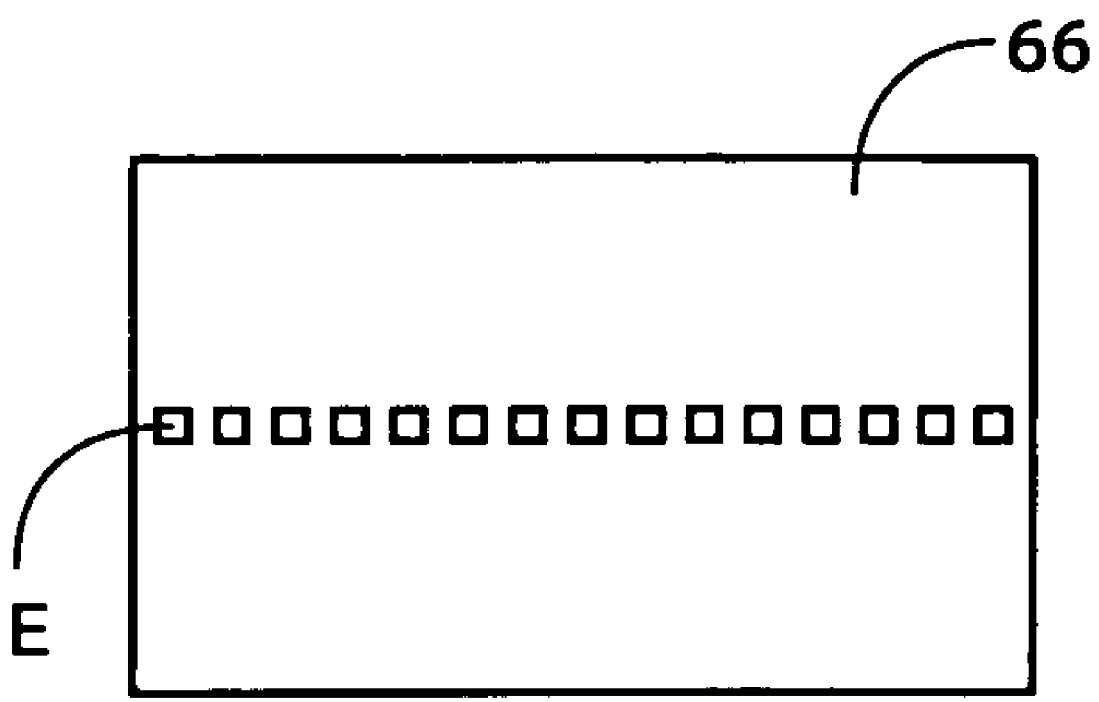
FIG. 4 is a view showing the press surface of the pulse wave sensor provided in the pressure pulse wave detecting probe of FIG. 3.

As shown in FIG. 4, a number of semiconductor pressure sensitive elements (hereinafter simply referred to as pressure sensitive elements) E are arranged on a press surface 66 of the above pressure pulse wave sensor 54 along a width direction of the radial artery 42, namely, in such a manner that an interval between them can be longer than a diameter of the radial artery 42 in a direction of moving the pressure pulse wave sensor 54 in parallel with the screw axis 44 and also in a constant space (for example, 0.2 mm apart from each other).

When the thus structured pressure pulse wave detecting probe 18 is pressed toward the radial artery 42 above the body surface 50 of the wrist 52, a pressure pulse wave sensor 54 detects a radial artery pulse wave RW produced from the radial artery 42 and transmitted to the body surface 50. As shown in FIG. 1, the pressure pulse wave signal SM representing the radial artery pulse wave is supplied through the A/D converter (not illustrated) to the electronic control device 32. In the following explanation, a pressure pulse wave signal SM outputted from the pressure pulse wave sensor 54 attached to the left wrist is designated as a left pressure pulse wave signal $SM_L$; a radial artery pulse wave RW represented by the left pressure pulse wave signal $SM_L$, as a left radial artery pulse wave $RW_L$; a pressure pulse wave signal SM outputted from the pressure pulse wave sensor 54 attached to the right wrist, as a right pressure pulse wave signal $SM_R$; and a radial artery pulse wave RW represented by the right pressure pulse wave signal $SM_R$, as a right radial artery pulse wave $RW_n$.

The electronic control device 32 is configured with a so called microcomputer provided with CPU 68, ROM 70, RAM 72 and I/O port (not illustrated) and others. In compliance with the program previously stored in the ROM 70, the CPU 68 utilizes the memory function of the RAM 72 and executes signal processing, thus outputting driving signals from the I/O port, controlling the pressure control valve 22 and the pneumatic pump 28 through a driving circuit (not illustrated) for attaining control of the cuff pressure PC, and outputting driving signals to the pneumatic pump 58 and the pressure control valve 60 through a driving circuit (not illustrated) for attaining adjustment of the pressure inside the pressure chamber 57 as well. Further, the CPU 68 is used to perform computations on the basis of signals supplied from the electronic control device 32, by which pulse-wave conduction time PCT and conduction time difference ΔPCT are calculated, and the thus calculated pulse-wave conduction time PCT and conduction time difference ΔPCT are displayed on a display 74 which serves as an output apparatus.

Figure 5:
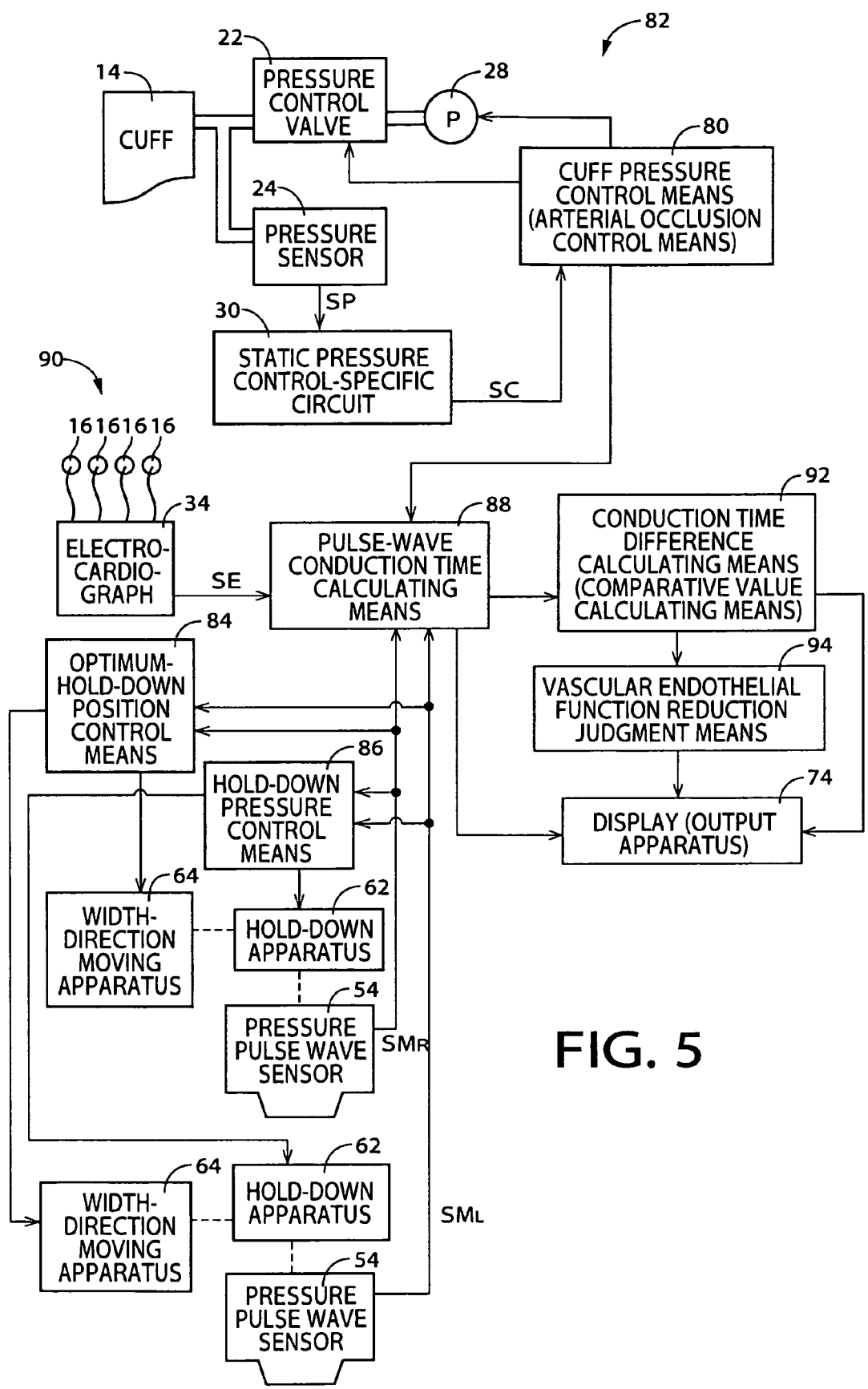
FIG. 5 is a functional block diagram explaining major control function of the CPU provided in the vascular endothelial function assessment apparatus of FIG. 1.

FIG. 5 is a functional block diagram explaining major control functions of the CPU 68 in the vascular endothelial function-assessing apparatus 10 as shown in FIG. 1. The cuff pressure controlling means 60 functioning as arterial occlusion controlling means judges the cuff pressure PC on the basis of the cuff pressure signal SC supplied from the static pressure valve-specific circuit 30 and controls the pressure control valve 22 and the pneumatic pump 28, thereby instantly elevating the cuff pressure PC up to a predetermined pressure level P1 (for example, 250 mmHg) which is higher than the highest blood pressure $BP_{SYS}$ at a site of wearing the cuff 14, followed by maintaining the cuff pressure PC for a predetermined time determined by a simulation (for example, for 5 minutes), and reducing the cuff pressure PC to an atmospheric pressure at a subsequent stage. Further, in the present embodiment, an arterial occlusion apparatus 82 is provided with the cuff 14, pressure control valve 22 for controlling the cuff pressure PC, pneumatic pump 28, pressure sensor 24 and cuff pressure controlling means 80. The arterial occlusion apparatus 82 is used to occlude arteries in the upper arm, and a reactive hyperemia then takes place at peripheral tissues downstream from a site of arterial occlusion when the occlusion is released, thereby increasing blood flow at arteries (namely, the brachial artery and connected arteries upstream or downstream therefrom) perfusing the tissues, which stimulates and induces endothelium-derived relaxing factors from vascular endothelium at the above specified regions or those where increased blood flow is found. Then, the arteries undergo dilation of the diameter after release of the endothelium-derived factors.

An optimum-hold-down position control means 84 is used to judge whether or not hold-down pressure position changing conditions can be attained on the basis of the fact that, of plural pressure sensitive elements E provided on a pressure pulse wave sensor 54, an element that can detect a maximum pressure (hereinafter the element is referred to as maximum pressure detecting element EM) is positioned at a site corresponding to a predetermined number or a distance from an edge of the arrangement used as a reference. Then, when the hold-down pressure position changing conditions are attained, the following hold-down pressure position changing operations are carried out. More particularly, in the hold-down pressure position changing operations, the pressure pulse wave sensor 54 is temporarily separated from the body surface 50, the width-direction moving apparatus 64 is used to move a hold-down apparatus 62 and a pressure pulse wave sensor 54 at a specified distance and then the hold-down apparatus 62 is used to press the pressure pulse wave sensor 54 by exerting a relatively small predetermined first hold-down pressure HDP1. Then, judgment is made again as to whether or not the above hold-down pressure position changing conditions can be attained, with the status kept as it is, and the above operations and judgment procedures are carried out until the hold-down pressure position changing conditions are no longer attained, more particularly, the above maximum pressure detecting element EM is approximately positioned at the center of the arrangement. The predetermined number or predetermined distance from an edge of the arrangement under the above hold-down pressure position changing conditions is determined on the basis of a diameter of the artery (radial artery 42 in the present embodiment) pressed by the pressure pulse wave sensor 54, for example, it will be set to be ¼ of the diameter.

Figure 6:
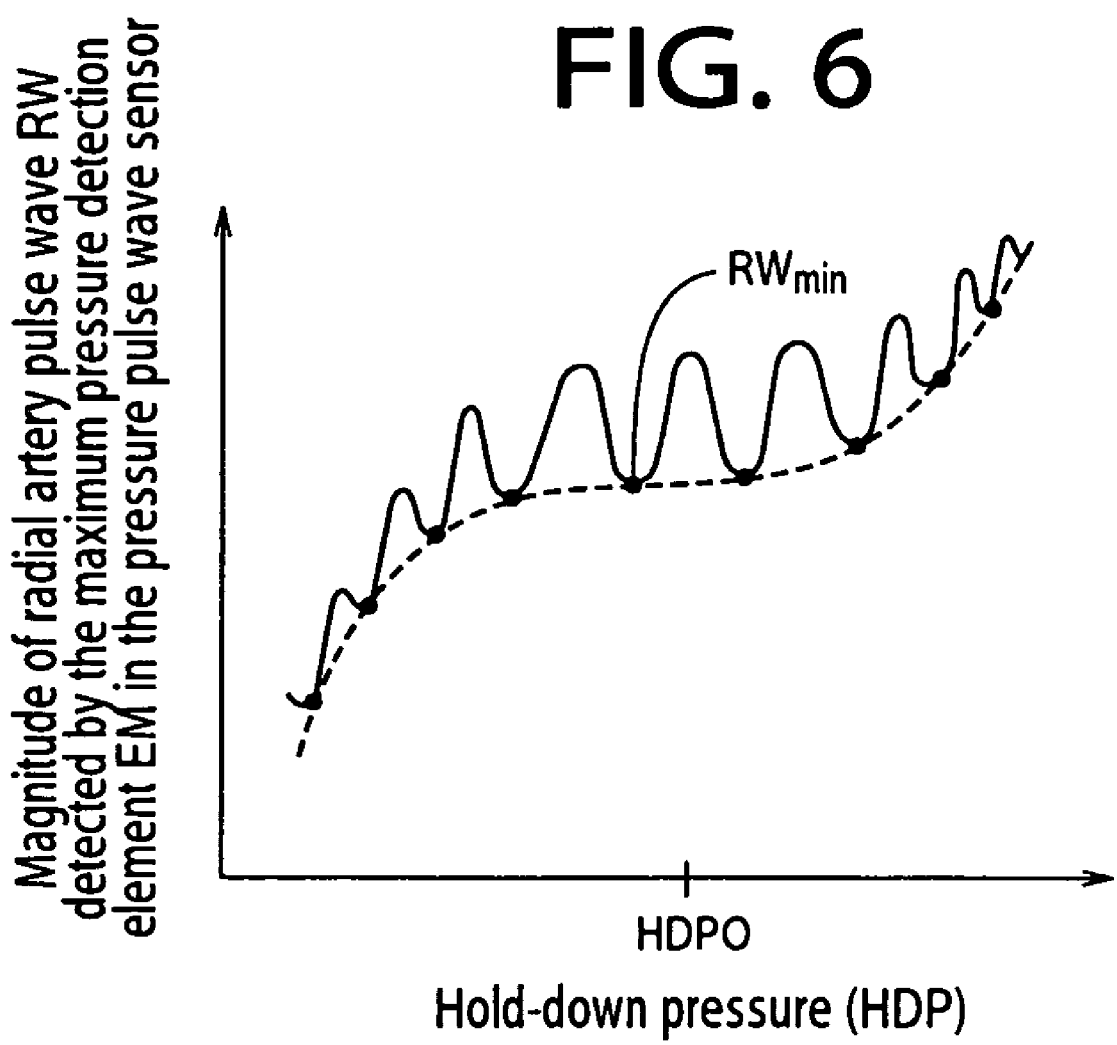
FIG. 6 is a view explaining the optimum hold-down pressure HDPO determined by the hold-down pressure control means of FIG. 5.

In an hold-down pressure control means 86, the pressure pulse wave sensor 54 is positioned at an optimally pressed site by the optimum-hold-down position control means 84, and the hold-down apparatus 62 is then used to allow hold-down pressure HDP of the pressure pulse wave sensor 54 to change successively according to pulsation in a predetermined hold-down pressure range or allow the hold-down pressure to change continuously at a relatively mild and constant rate in a predetermined hold-down pressure range. An optimum hold-down pressure HDPO is determined on the basis of the radial artery pulse wave RW obtained in the course of changes in the hold-down pressure HDP, and the hold-down apparatus 62 is used to maintain the hold-down pressure HDP of the pressure pulse wave sensor 54 in a range of an optimum hold-down pressure HDPO. In this instance, the optimum hold-down pressure HDPO is designated as a hold-down pressure by which the side pressed by the pressure pulse wave sensor 54 on a blood vessel wall of the radial artery 42 derived from the hold-down pressure HDP of the pressure pulse wave sensor 54 is rendered almost flat. For example, as shown in FIG. 6, the HDPO is a hold-down pressure value in a specified range, a center of which is in the middle of a flat area formed by the curve (shown by the dotted line in FIG. 6) connected with a lower peak value (rising point) $RW_{min}$ of the radial artery pulse wave RW in a two-dimensional graph showing the size of the radial artery pulse wave RW obtained from a maximum pressure detecting element EM of the pressure pulse wave sensor 54 and the hold-down pressure HDP of the pressure pulse wave sensor 54, when the hold-down pressure HDP is increased continuously in a range containing a sufficient optimum hold-down pressure HDPO.

A pulse-wave conduction time calculating means 88 is used to calculate respectively the right pulse-wave conduction time $PCT_R$ which is a conduction time of a pulse wave from the heart to the right wrist and the left pulse-wave conduction time $PCT_L$ which is a conduction time of a pulse wave from the heart to the left wrist, on the basis of electrocardiographic signal SE supplied successively from the electrocardiograph 34 and the right pressure pulse wave signal $SM_R$ and the left pressure pulse wave signal $SM_L$ supplied successively from the respective maximum pressure detecting elements EM of two pressure pulse wave sensors 54. Namely, a difference between the time when a specified site (R-wave in this embodiment) of the electrocardiogram represented by the electrocardiographic signal SE is detected and the time when a specified site (rising point in this embodiment) of the right radial artery pulse wave $RW_R$ represented by the right pressure pulse wave signal $SM_R$ is detected is calculated as the right pulse-wave conduction time $PCT_R$, whereas a difference between the time when a specified site (R-wave) of the electrocardiogram represented by the electrocardiographic signal SE is detected and the time when a specified site (rising point) of the left radial artery pulse wave $RW_L$ represented by the pressure pulse wave signal $SM_l$ is detected is calculated as the left pulse-wave conduction time $PCT_L$. Specifically, the pulse-wave conduction time PCT calculated on the basis of the electrocardiogram is a conduction time of a pulse wave from the heart to the right (left) wrist to which pre-ejection period from the time when the cardiac muscle starts to contract to the time when blood is ejected is added.

In the pulse-wave conduction time calculating means 88, as explained above, the right pulse-wave conduction time $PCT_R$ and the left pulse-wave conduction time $PCT_L$ are calculated over time respectively in terms of values for each pulse or an average of a few pulses by referring to a period from the time when the cuff pressure PC is controlled by the cuff pressure control means 80 and arteries in the left upper arm are occluded by the cuff 14 at a specified time (before 5 minutes in this embodiment) to the time when a specified time has passed after the arterial occlusion is released (5 minus in this embodiment) Since no left radial artery pulse wave $RW_L$ takes place while the arteries are occluded in the left upper arm, no calculation can be made for the left pulse-wave conduction time $PCT_L$. Changes over time in the thus calculated right pulse-wave conduction time $PCT_R$ and the left pulse-wave conduction time $PCT_L$ are displayed graphically on the display 74.

In this embodiment, the first segment covers an area from the heart to the left wrist and the second segment covers an area from the heart to the right wrist. The above left pulse-wave conduction time $PCT_L$ and the right pulse-wave conduction time $PCT_R$ respectively correspond to the first pulse-wave-conduction-velocity-relating information and the second pulse-wave-conduction-velocity-relating information. The electrocardiograph 34, two pressure pulse wave sensors 54, optimum-hold-down position control means 84, hold-down pressure control means 86 and pulse-wave conduction time calculating means 88 give functions as a pulse-wave-conduction-velocity-relating information measurement apparatus 90.

When the first segment covering an area from the heart to the left wrist is compared with the second segment covering an area from the heart to the right wrist, it is found that these two segments are almost symmetrical with respect to the median plane of the patient 12. Since the aortic artery and its branches are not symmetrical, these two segments are not completely symmetrical with respect to the median plane.

A conduction time difference calculating means 92, which functions as comparative value calculating means, is to calculate the conduction time difference ΔPCT corresponding to the comparative value, on the basis of the pulse-wave conduction time PCT calculated over time in terms of a value for each pulse or an average of a few pulses in the above pulse-wave conduction time calculating means 88. Changes over time in the thus calculated conduction time difference ΔPCT are displayed graphically on the display 74. The above conduction time difference ΔPCT can be obtained by subtracting the time-corresponding right pulse-wave conduction time $PCT_R$ from the left pulse-wave conduction time $PCT_L$ calculated by the pulse-wave conduction time calculating means 88, representing a difference in these two pulse-wave conduction times $PCT_L$ and $PCT_R$ based on the same pulsation or point in time.

FIG. 7 through FIG. 10 are graphs showing the right pulse-wave conduction time $PCT_R$ and the left pulse-wave conduction time $PCT_L$ calculated by the pulse-wave conduction time calculating means 88 as well as the conduction time difference ΔPCT calculated by the conduction time difference calculating means 92. In FIG. 7 through FIG. 10, measurement is carried out in different patients, and the left brachial artery is occluded for 5 minutes, which corresponds to a part from 5 to 10 minutes in the graph. As shown in these graphs, the left pulse-wave conduction time $PCT_L$ shows spontaneous variations, although such variations vary among individuals. Thus, no clear changes after the release from ischemia are obtained for the left pulse-wave conduction time $PCT_L$ itself. The right pulse-wave conduction time $PCT_R$ for the second segment, which is almost symmetrical to the segment for measuring the left pulse-wave conduction time $PCT_L$ with respect to the median plane, shows the spontaneous variations similar to those observed in the left pulse-wave conduction time $PCT_L$. This indicates that these spontaneous variations reflect the effects of systemic factors common to the both sides of body. Therefore, conduction time difference ΔPCT is free from the variations due to the influence of the systemic factors.

Prior to an explanation about the assessment of vascular endothelial function based on the conduction time difference ΔPCT, changes in the pulse-wave conduction time PCT with reactive hyperemia will be explained by referring to the Moens-Korteweg formula as shown in Expression 1.

$$PWV = (Eh/2\rho R)^{1/2} \quad \text{(Expression 1)}$$

wherein E represents Young's modulus; h, thickness of blood vessel wall; ρ, density of blood; and R, radius of a blood vessel.

This is a well known formula regarding pulse wave conduction velocity PWV, by which Expression 2 can be obtained by referring to the relationship between the pulse wave conduction velocity PWV and the pulse-wave conduction time PCT.

$$PCT = D/PWV = D(2\rho R)^{1/2}/(Eh)^{1/2} \quad \text{(Expression 2)}$$

wherein D represents conduction distance.

Expression 2 shows that an increase in blood vessel radius R, a decrease in blood vessel wall thickness h, and a decrease in elasticity E result in a longer pulse-wave conduction time PCT.

When vascular endothelial function is normal and blood flow is increased in the arm to which the cuff 14 is attached due to the reactive hyperemia, endothelium-derived relaxing factors are released from the vascular endothelium to cause dilation of blood vessels (increase in the radius and decrease in the wall thickness) and lower the elasticity of blood vessels in association with the dilation at a blood flow-increased area, thus resulting in an increase in the pulse-wave conduction time PCT (delayed). However, when vascular endothelial function is impaired, blood vessels will not dilate nearly as much on reactive hyperemia and the pulse-wave conduction time PCT will not increase nearly as much either. It is therefore possible to evaluate vascular endothelial function at the segment where the left pulse-wave conduction time $PCT_L$ is measured (or segment from the heart to the left wrist) by referring to the extent of the increase in the left pulse-wave conduction time $PCT_L$ due to the reactive hyperemia. As shown in FIG. 7 through FIG. 10, the left pulse-wave conduction time $PCT_L$ shows large spontaneous variations, which makes it difficult to judge the extent of the increase with the reactive hyperemia. However, the conduction time difference ΔPCT is free from the spontaneous variations and therefore an increase in the pulse-wave conduction time with the reactive hyperemia can be clearly detected.

Figure 7:
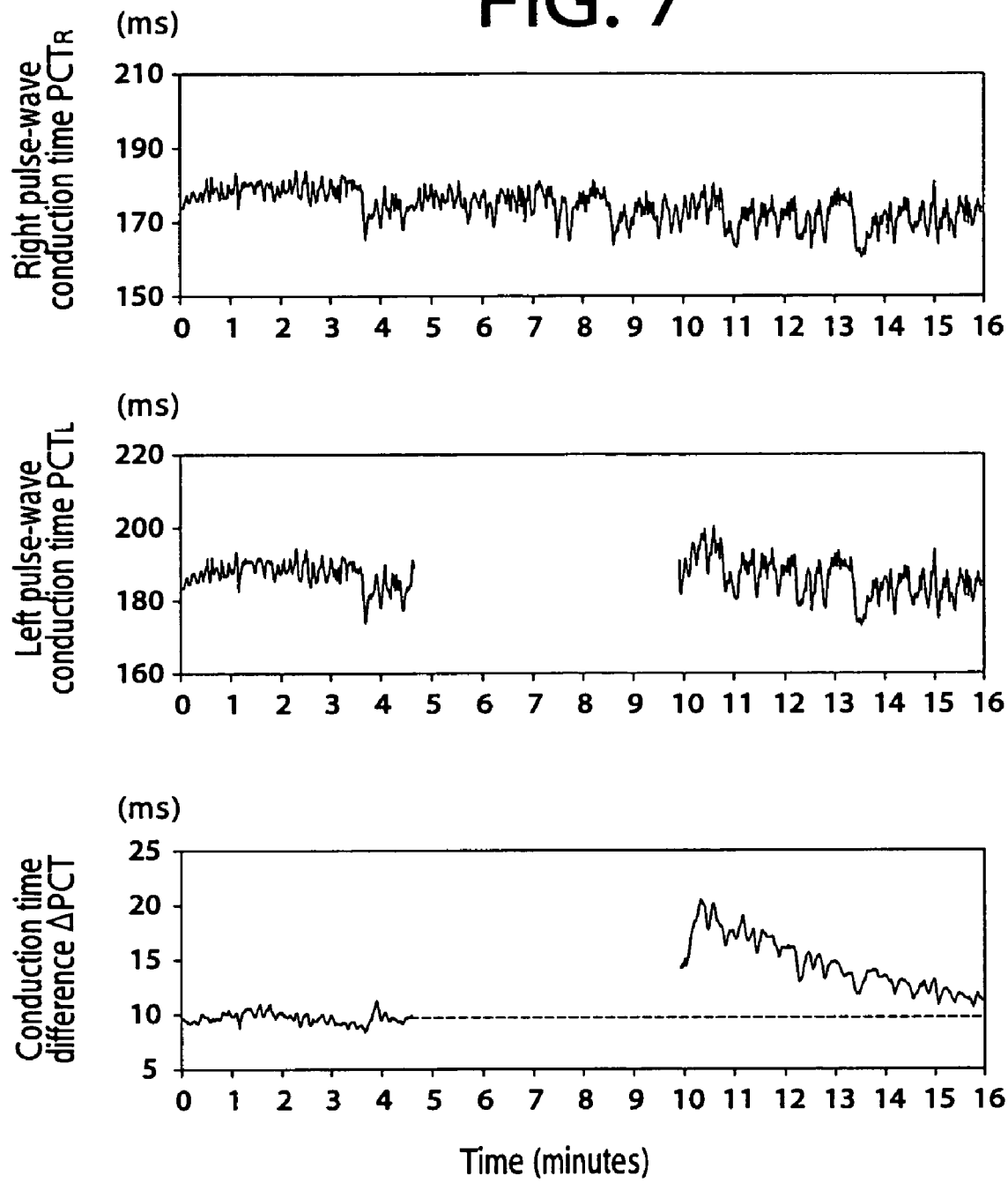
FIG. 7 is a view showing the right pulse-wave conduction time, left pulse-wave conduction time and conduction time difference calculated by the pulse-wave conduction time calculating means and conduction time difference calculating means of FIG. 5.
Figure 8:
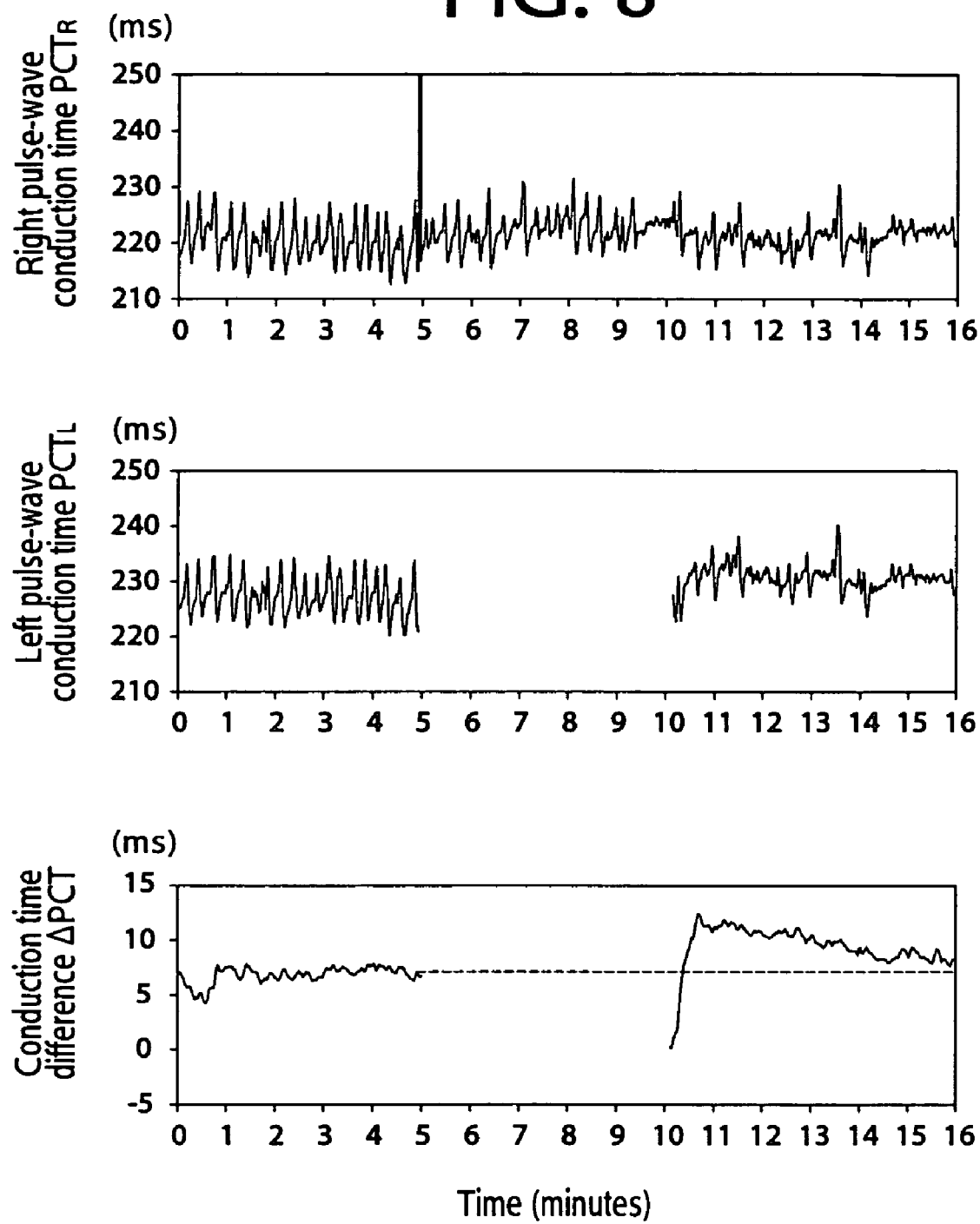
FIG. 8 is a view showing the right pulse-wave conduction time, left pulse-wave conduction time and conduction time difference calculated by the pulse-wave conduction time calculating means and conduction time difference calculating means of FIG. 5.
Figure 9:
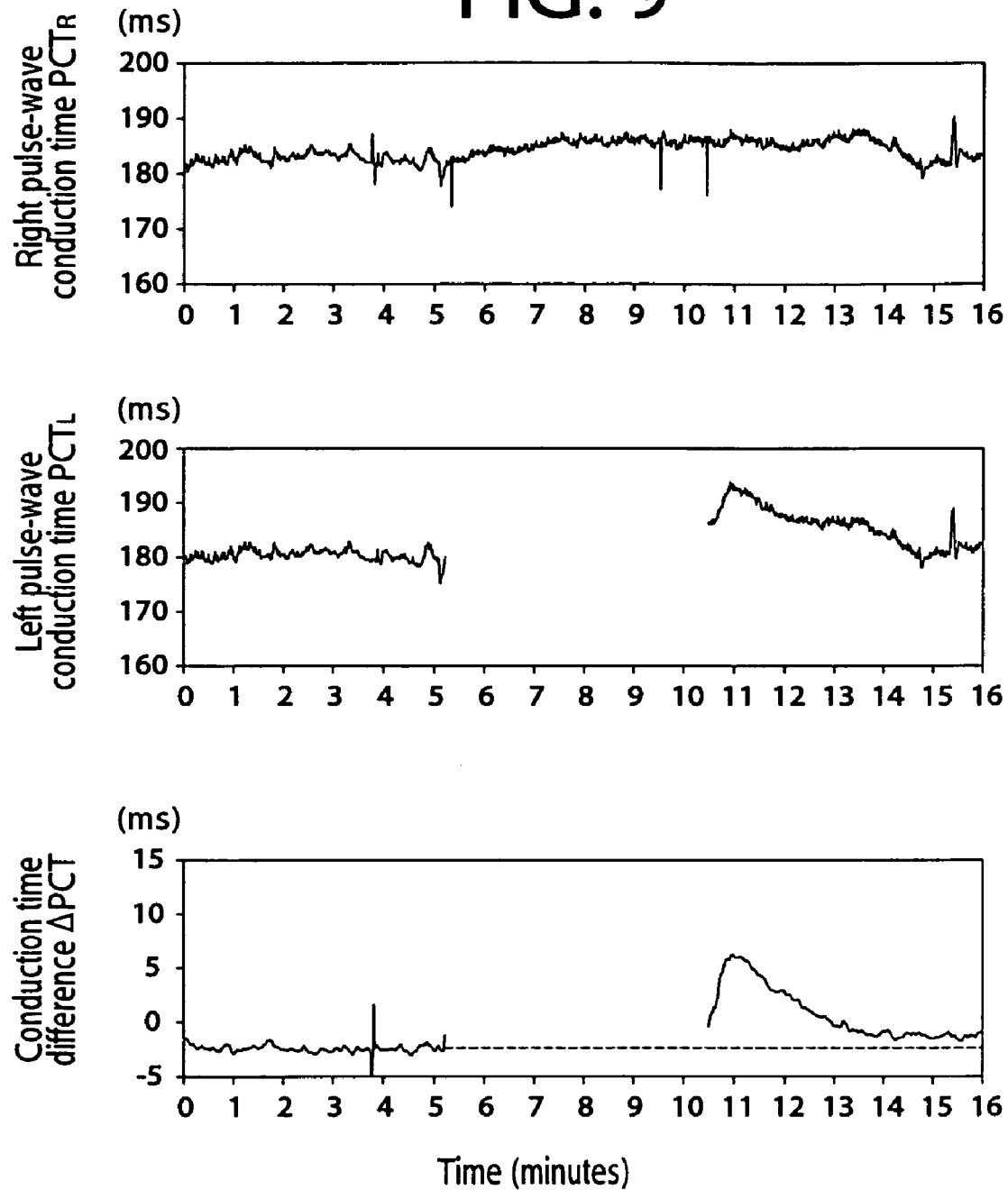
FIG. 9 is a view showing the right pulse-wave conduction time, left pulse-wave conduction time and conduction time difference calculated by the pulse-wave conduction time calculating means and conduction time difference calculating means of FIG. 5.
Figure 10:
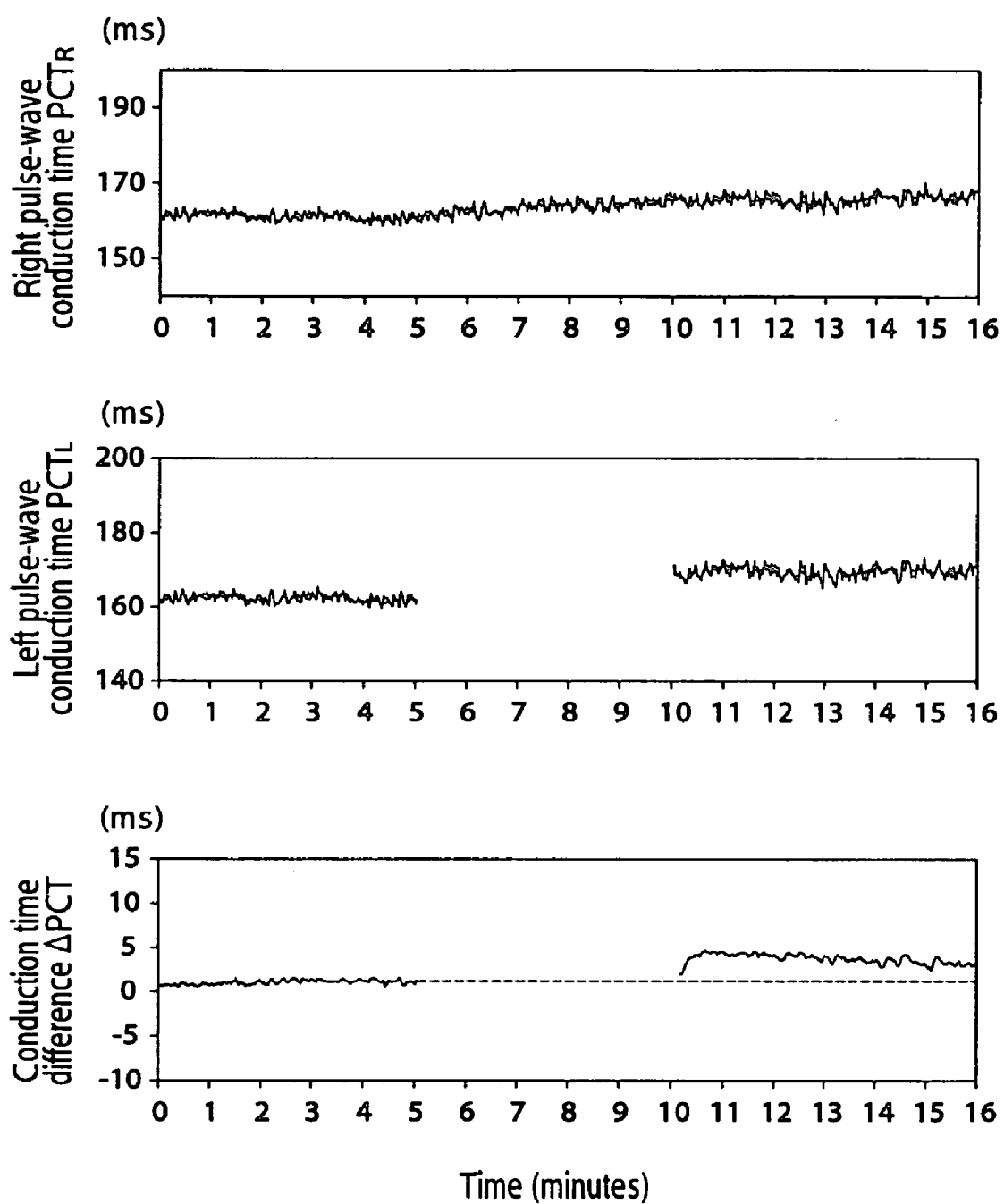
FIG. 10 is a view showing the right pulse-wave conduction time, left pulse-wave conduction time and conduction time difference calculated by the pulse-wave conduction time calculating means and conduction time difference calculating means of FIG. 5.

There may be many ways for evaluating changes in conduction time difference ΔPCT with reactive hyperemia. The evaluation can be made on the basis of, for example, an increased quantity in the peak of the conduction time difference ΔPCT after the release from ischemia in relation to the conduction time difference ΔPCT before the ischemia or an increased rate of the peak of the conduction time difference ΔPCT after the release from the ischemia in relation to the conduction time difference ΔPCT before the ischemia. Where the increased quantity and increased rate are large, vascular endothelial function is judged to be normal. In the patients shown in FIG. 7 through FIG. 10, those in FIG. 7 through FIG. 9 are judged normal in the vascular endothelial function whereas those in FIG. 10 are judged abnormal in the vascular endothelial function.

When reverting to FIG. 5, in vascular endothelial dysfunction judgment means 94, the conduction time difference ΔPCT after the release from ischemia calculated by the conduction time difference calculating means 92 is referred to determine the peak value, and the conduction time difference ΔPCT before start of the ischemia is subtracted from the peak value to obtain a difference between the conduction time difference ΔPCT before the ischemia and that after the ischemia, or the peak value is divided by the conduction time difference ΔPCT before the start of the ischemia to calculate the ratio of the conduction time difference ΔPCT before the ischemia to that after the ischemia (the difference or the ratio in this instance must always be positive). Where the thus obtained difference and ratio are at or less than a predetermined judgment standard value established by simulations, it is judged that they show an impairment of vascular endothelial function. In this instance, character r symbols showing such an impairment are displayed on the display 74. A value obtained at one specified point (for example, immediately before the start of ischemia) may be used in calculating the conduction time difference ΔPCT before start of ischemia. In this embodiment, an average value obtained for a certain time before the start of ischemia (for example, 3 minutes) is used to remove variation in the value.

Figure 11:
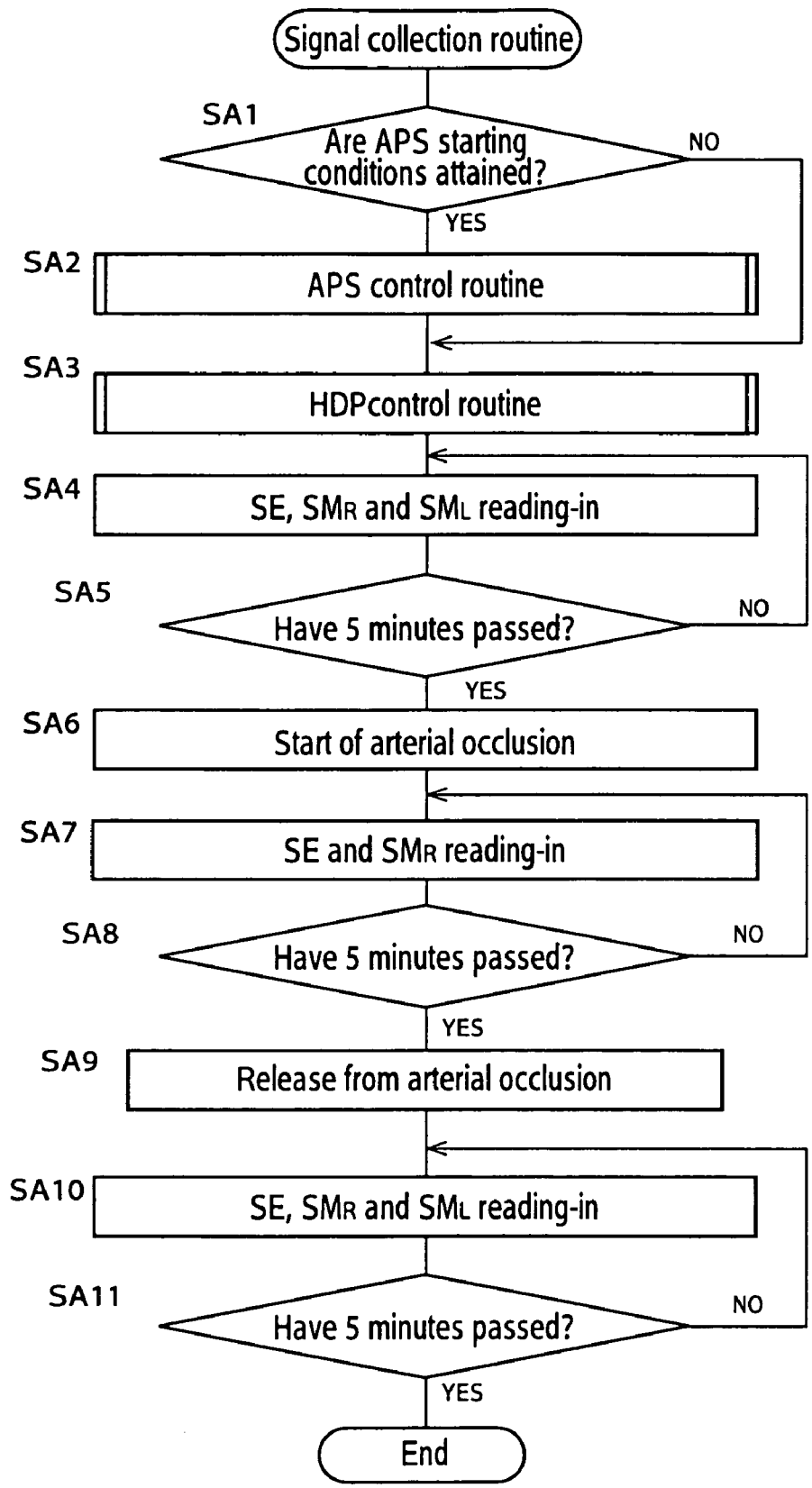
FIG. 11 is a flowchart describing major control operations of the CPU in the functional block diagrams of FIG. 5, showing a signal collection routine.
Figure 12:
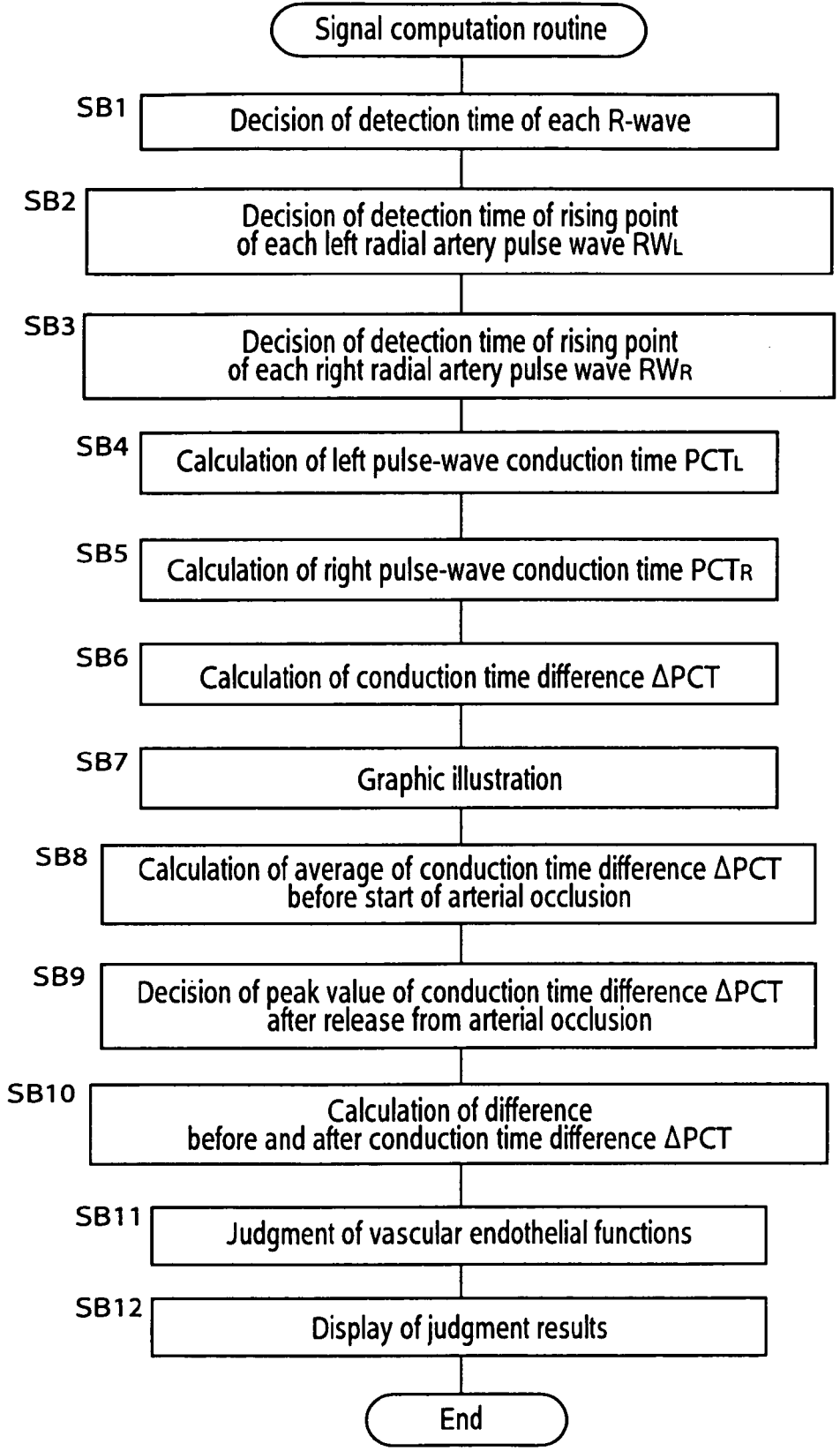
FIG. 12 is a flowchart describing the major control operations of the CPU in the functional block diagrams of FIG. 5, showing a signal computation routine.

FIG. 11 and FIG. 12 are flowcharts showing major control operations of the CPU 68 indicated in the functional block diagram of FIG. 5. FIG. 11 illustrates a signal collecting routine and FIG. 12 illustrates a signal computation routine.

In step SA1 of FIG. 11 (hereinafter, the word, step, is omitted), judgment is made as to whether hold-down position changing conditions (APS starting conditions) are attained or not under conditions where, of pressure sensitive elements E arranged on the press surface 66 of pressure pulse wave sensor 54, the maximum pressure detecting element EM is positioned at a specified number or specified distance from the arrangement. When this judgment is denied, steps after SA3 to be described later will be carried out.

In contrast, when the judgment on SA1 is affirmed, namely, where the pressure pulse wave sensor 54 is positioned inappropriate in relation to the radial artery 42, APS control routine for SA2 is carried out, which is equivalent to the optimum-hold-down position control means 84. In the APS control routine, the width-direction moving apparatus 64 is controlled to determine an optimum hold-down position so that, of individual pressure detecting elements E in the pressure pulse wave sensor 54, a pressure detecting element E which is able to detect a maximum amplitude is positioned approximately at the center of the arrangement of the pressure detecting elements E, and this pressure detecting element E is designated as the maximum pressure detecting element EM. The pressure pulse wave signal SM explained below means a pressure pulse wave signal SM detected by the maximum pressure detecting element EM determined in this step of SA2.

Where judgment is made on the SA1 as explained above or the above SA2 is carried out, HDP control routine for SA3 which is equivalent to the hold-down pressure control means 86 is carried out as a subsequent step. More particularly, the pressure control valve 60 is controlled to elevate continuously the hold-down pressure HDP of the pressure pulse wave sensor 54, during which a hold-down pressure which attains the maximum amplitude of the radial artery pulse wave RW detected by the maximum pressure detecting element EM is designated as an optimum hold-down pressure HDPO, and the hold-down pressure HDP of the pressure pulse wave sensor 54 is retained in the optimum hold-down pressure HDPO.

In the subsequent SA4, electrocardiographic signal SE, right pressure pulse wave signal $SM_R$ and left pressure pulse wave signal $SM_L$ are read in for every sampling period at a specified point in time. Then, in SA5, judgment is made as to whether or not 5 minutes passed after the start of reading the signals at SA4. Where judgment on the SA5 is denied, the SA4 will be repeated to continue reading of the electrocardiographic signal SE, right pressure pulse wave signal $SM_R$ and left pressure pulse wave signal $SM_L$. These steps of SA4 and SA5 will function as a pre-stimulation measurement step in combination with the SB1 through SB5 (FIG. 12) to be described later and used for calculating the left pulse-wave conduction time $PCT_L$ and the right pulse-wave conduction time $PCT_R$ on the basis of signals obtained in SA4 and SA5.

Where judgment on the SA5 is affirmed, steps from SA6 through SA9 corresponding to the stimulation step will be carried out. In SA6, the cuff pressure signal SC is at first referred to judge the cuff pressure PC and control the pneumatic pump 28 and the pressure control valve 22, thereby controlling the cuff pressure PC within the previously described pressure value P1 to start arterial occlusion on the left upper arm.

In the subsequent SA7, electrocardiographic signal SE and right pressure pulse wave signal $SM_R$ are read in for every sampling period at a specified point in time. Then, in SA8, judgment is made as to whether or not 5 minutes passed after the start of arterial occlusion. Where this judgment is denied, the SA7 will be repeated to continue reading of the electrocardiographic signal SE and the right pressure pulse wave signal $SM_R$. Where judgment on SA8 is affirmed, the pneumatic pump 28 is stopped to control the pressure control valve 22, thereby reducing the cuff pressure PC down to an atmospheric pressure to release arterial occlusion. Once the arterial occlusion is released, a reactive hyperemia takes place at tissues peripheral to a site of arterial occlusion and results in an increase in arterial blood perfusing through the tissues, which stimulates to induce the release of endothelium-derived relaxing factors from vascular endothelium at an area where blood flow has increased.

In the subsequent SA10, as with the SA4, the electrocardiographic signal SE, right pressure pulse wave signal $SM_R$ and left pressure pulse wave signal $SM_L$ are read in for every sampling at a specified point in time. Then, in SA11, judgment is made as to whether or not 5 minutes passed after the start of reading the signals in SA10 after the release from arterial occlusion. Where this judgment is denied, the SA10 will be repeated to continue reading of the electrocardiographic signal SE, right pressure pulse wave signal $SM_R$ and left pressure pulse wave signal $SM_L$. These SA10 and SA11 will function as a post-stimulation measurement step in combination with the SB1 through SB5 (FIG. 12) to be described later and used for calculating the left pulse-wave conduction time $PCT_L$ and the right pulse-wave conduction time $PCT_R$ on the basis of signals obtained in SA10 and SA11.

In contrast, where judgment on the SA11 is affirmed, the signal collecting routine is completed to carry out the signal computation routine as shown in FIG. 12.

In conducting the signal computation routine as shown in FIG. 12, an electrocardiogram represented by the electrocardiographic signal SE read in the steps of SA4, SA7 and SA10 is referred to determine a detection time of R-wave for each pulse in the initial step of SB1, and an electrocardiogram represented by the left pulse wave signal $SM_L$ read in the steps of SA4, SA7 and SA10 is referred to determine a rising point of the left radial artery pulse wave $RW_L$ for each pulse in the subsequent SB2, and an electrocardiogram represented by the right pulse wave signal $SM_R$ read in the steps of SA4, SA7 and SA10 is referred to determine a rising point of the right radial artery pulse wave $RW_R$ for each pulse in the next step of SB3.

Then, in the subsequent SB4, a difference between the detection time of individual electrocardiogram R-waves determined in SB1 and the detection time of rising points of individual left radial artery pulse waves $RW_L$ determined in SB2 is referred to calculate over time the left pulse-wave conduction time $PCT_L$ in terms of a value for each pulse or an average of a few pulses, and in the subsequent SB5 a difference between the detection time of individual electrocardiogram R-waves determined in SB1 and the detection time of the individual right radial artery pulse waves $RW_R$ determined in SB3 is referred to calculate over time the right pulse-wave conduction time $PCT_R$ in terms of a value for each pulse or an average of a few pulses.

In the subsequent SB6 equivalent to the conduction time difference calculating means 92 and the comparative value calculation step, the right pulse-wave conduction time $PCT_R$ calculated in SB5 is subtracted from the left pulse-wave conduction time $PCT_L$ calculated in SB4 to calculate over time the conduction time difference $\Delta PCT$ 5 minutes before ischemia (namely, pre-ischemic comparative value) and the conduction time difference $\Delta PCT$ 5 minutes after ischemia (namely, post-ischemic comparative value) in terms of a value for each pulse or an average of a few pulses.

In the subsequent SB7, changes over time in the left pulse-wave conduction time $PCT_L$, right pulse-wave conduction time $PCT_R$ and conduction time difference $\Delta PCT$ calculated in the above SB4 through SB6 are illustrated graphically as shown in FIG. 7 through FIG. 10.

Then, the steps of SB8 through SB12 equivalent to the vascular endothelial dysfunction judgment means 94 and vascular endothelial dysfunction judgment step will be carried out. In the SB8, with regard to values of the conduction time difference $\Delta PCT$ 5 minutes before ischemia calculated in SB6, those of conduction time difference $\Delta PCT$ 3 minutes before ischemia are averaged. Then, in SB9, a peak of the conduction time difference $\Delta PCT$ after the release from ischemia calculated in SB6 is determined. Thereafter, in the subsequent SB10, the average of the conduction time difference $\Delta PCT$ 3 minutes before ischemia calculated in SB8 is subtracted from the peak of the conduction time difference $\Delta PCT$ after the release from ischemia determined in SB9 to calculate the difference between the conduction time difference $\Delta PCT$ before ischemia and that after ischemia.

Then, in SB11, where a difference between the conduction time difference $\Delta PCT$ before ischemia and that after ischemia calculated in the above SB10 is at or lower than the predetermined judgment standard value, the vascular endothelial function are judged to be impaired, and where the difference is greater than the predetermined judgment standard value, the vascular endothelial function is judged to be normal. In SB12, the message showing the judgment results will be displayed on the display 74.

According to the above embodiment, the left pulse-wave conduction time $PCT_L$ measured by the pulse-wave-conduction-velocity-relating information measurement apparatus 90 after the release from ischemia (arterial occlusion) by the arterial occlusion apparatus 82 is affected by dilation of the vessels and reduced elasticity of the vessel walls due to the flow-mediated dilation response after the release from ischemia undergoes changes in the left pulse-wave conduction time $PCT_L$ measured before ischemia. However, the left pulse-wave conduction time $PCT_L$ by itself shows spontaneous variations, which obscure the changes with reactive hyperemia. However, in this embodiment where a right pulse-wave conduction time $PCT_R$ is measured, the right pulse-wave conduction time $PCT_R$ is a pulse-wave conduction time PCT for the second segment almost symmetrical to the first segment with respect to the median plane and therefore similar to the left pulse-wave conduction time $PCT_L$ in spontaneous variations due to the influences of systemic factors. Further, since the conduction time difference ΔPCT calculated by the conduction time difference calculating means 92 (SB6) is a difference between the left pulse-wave conduction time $PCT_L$ and the right pulse-wave conduction time $PCT_R$, the conduction time difference ΔPCT is free of spontaneous variations due to the influences of systemic fluctuations in blood pressure, heart rate and other factors. Therefore, since comparison of the conduction time difference ΔPCT before ischemia with that after ischemia would make clear the change in the left pulse-wave conduction time $PCT_L$ with reactive hyperemia, the vascular endothelial function can be assessed at a high reliability by referring to the assessment of vascular endothelial function on the basis of comparison of the conduction time difference ΔPCT before ischemia with that after ischemia. In addition, measurement of the pulse-wave conduction time PCT does not require a great amount of skill and is advantageous in that the apparatus is inexpensive.

According to the above embodiment, the vascular endothelial dysfunction judgment means 94 (from SB8 through SB12) is used to make an automatic judgment of the vascular endothelial dysfunction on the basis of the fact that a difference between the peak of the conduction time difference ΔPCT after the release from ischemia calculated by the conduction time difference calculating means 92 (SB6) and the conduction time difference ΔPCT before ischemia is at or lower than a predetermined judgment standard value.

Further, according to the above embodiment, since the vascular endothelial dysfunction judgment means 94 is provided with the display 74 which graphically illustrates changes over time in the conduction time difference ΔPCT calculated by the conduction time difference calculating means 92 (SB6), it is able to determine easily a point in time when the blood vessel dilated to the greatest extent by referring to graphically illustrated changes over time in the conduction time difference ΔPCT.

In the above embodiment, the first segment covers an area from the heart to the wrist 52 in which arteries are occluded by the arterial occlusion apparatus 82, or including a relative long area from the heart to the wrist 52. The first segment has accordingly a longer pulse-wave conduction time PCT. Thus, since the conduction time difference ΔPCT calculated by the conduction time difference calculating means 92 (SB6) has a greater change after the release from ischemia than that before ischemia, it is possible to examine the vascular endothelial function at a higher reliability.

Next, an explanation will be made about the second embodiment of the invention. In making an explanation about the second embodiment, parts having the same structure with the first embodiment will be given the same symbol and omitted from explanation.

The second embodiment is different from the first embodiment only in that calculation is made for the conduction time ratio R (PCT) in place of the conduction time difference ΔPCT of the first embodiment, providing similar effects as in the first embodiment. Hereinafter an explanation will be made about the difference between the first embodiment and the second embodiment.

Figure 13:
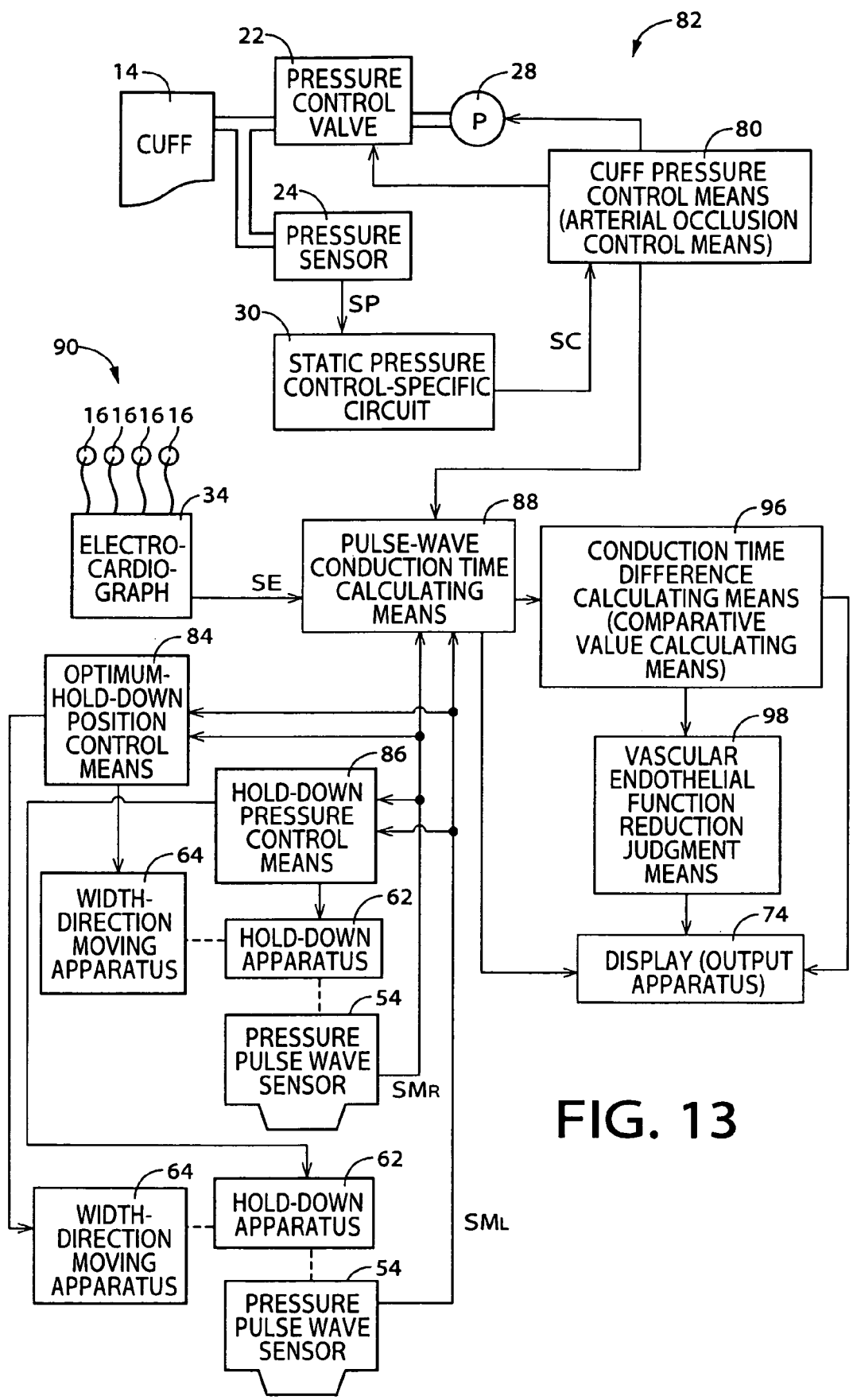
FIG. 13 is a functional block diagram explaining major control function of the CPU provided in the vascular endothelial function assessment apparatus of the second embodiment of the invention.

FIG. 13 is a functional block diagram describing major control functions of the CPU 68 in the vascular endothelial function assessment apparatus of the second embodiment. The conduction time ratio calculating means 96 which functions as comparative value calculating means is used to calculate a ratio of the conduction time PCT based on mutually equal pulsations or points in time, namely, conduction time ratio R (PCT), by dividing the left pulse-wave conduction time $PCT_L$ by the right pulse-wave conduction time $PCT_R$, each of which is calculated over time in terms of a value for each pulse or an average of a few pulses by the pulse-wave conduction time calculating means 88. Changes over time in the thus calculated conduction time ratio R (PCT) are displayed graphically on the display 74.

Figure 14:
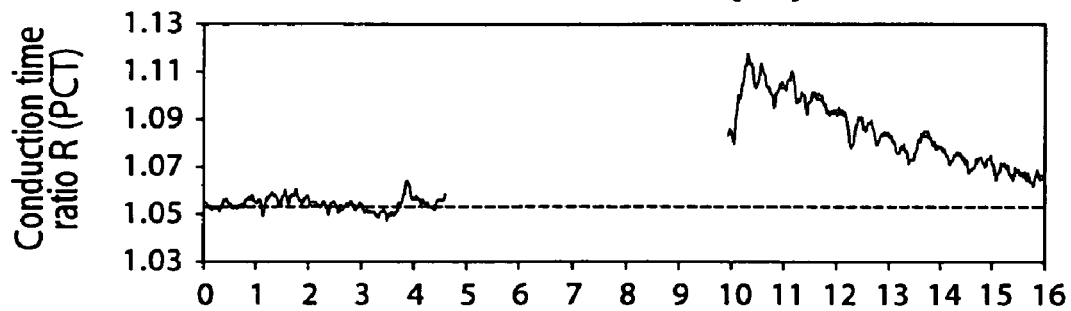
FIG. 14 is a view showing changes overtime in the conduction time ratio R (PCT) calculated by the left pulse-wave conduction time $PCT_L$ and right pulse-wave conduction time $PCT_R$ of FIG. 7 through FIG. 10.
Figure 14:
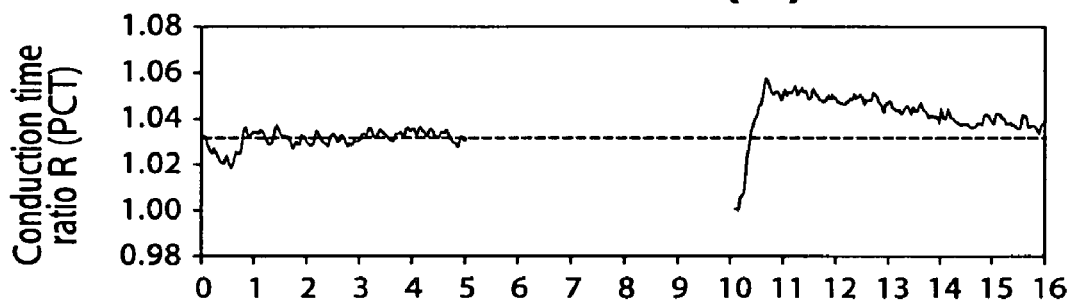
Figure 14:
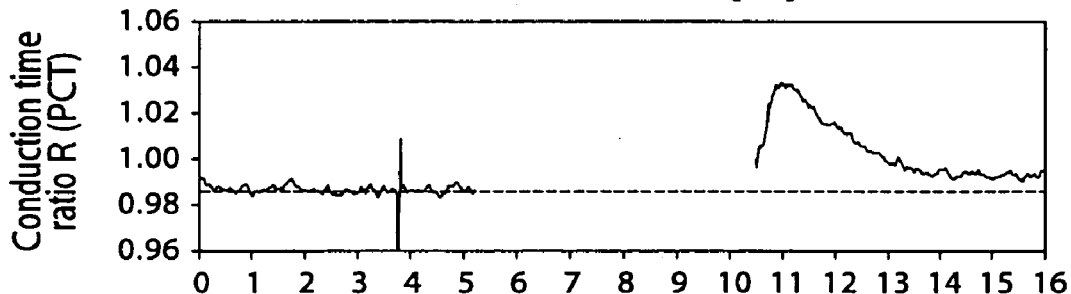
Figure 14:
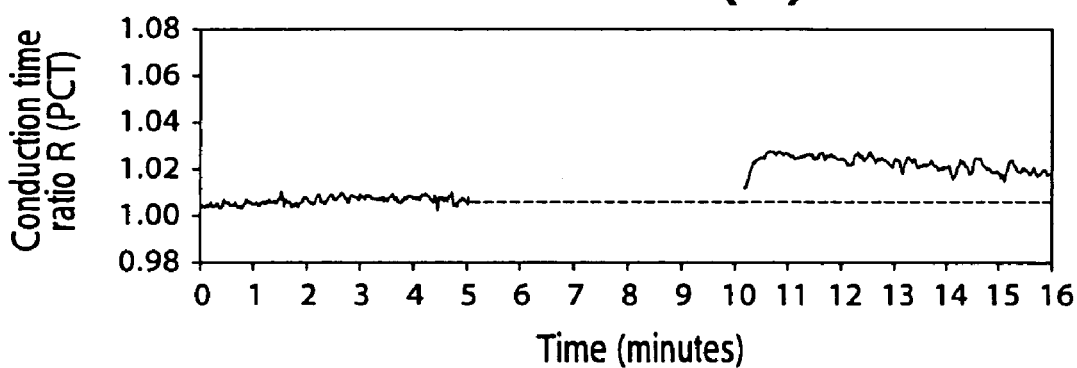

FIG. 14 is a view illustrating changes over time in the conduction time ratio R (PCT) calculated by the left pulse-wave conduction time $PCT_L$ and the right pulse-wave conduction time $PCT_R$ shown in FIG. 7 through FIG. 10, wherein (a), (b), (c) and (d) represent changes over time in the conduction time ratio R (PCT) calculated by the left pulse-wave conduction time $PCT_L$ and the right pulse-wave conduction time $PCT_R$ respectively in FIG. 7, FIG. 8, FIG. 9 and FIG. 10. As apparent from the comparison of the graph shown in FIG. 14 with lower graphs shown in FIG. 7 through FIG. 10, it is found that the conduction time ratio R (PCT) is almost similar to the change with the conduction time difference ΔPCT.

When returning to FIG. 13, the vascular endothelial dysfunction judgment means 98 is different from the vascular endothelial dysfunction judgment means 94 of the first embodiment only in that the conduction time ratio R (PCT) is used in place of the conduction time difference ΔPCT. More particularly, the vascular endothelial dysfunction judgment means 98 is used to determine a peak value by referring to the conduction time ratio R (PCT) after the release from ischemia calculated by the conduction time ratio calculating means 96, and the conduction time ratio R (PCT) before start of ischemia is subtracted from the peak value to obtain a difference between the conduction time ratio R (PCT) before ischemia and that after ischemia, or the peak value is divided by the conduction time ratio R (PCT) before start of ischemia to obtain a ratio of the conduction time ratio R (PCT) before ischemia to that after ischemia. Where the thus obtained difference or ratio is at or lower than a predetermined judgment standard value determined by simulations, it is judged that the vascular endothelial function is impaired, and characters or symbols showing such impairment are displayed on the display 74.

Figure 15:
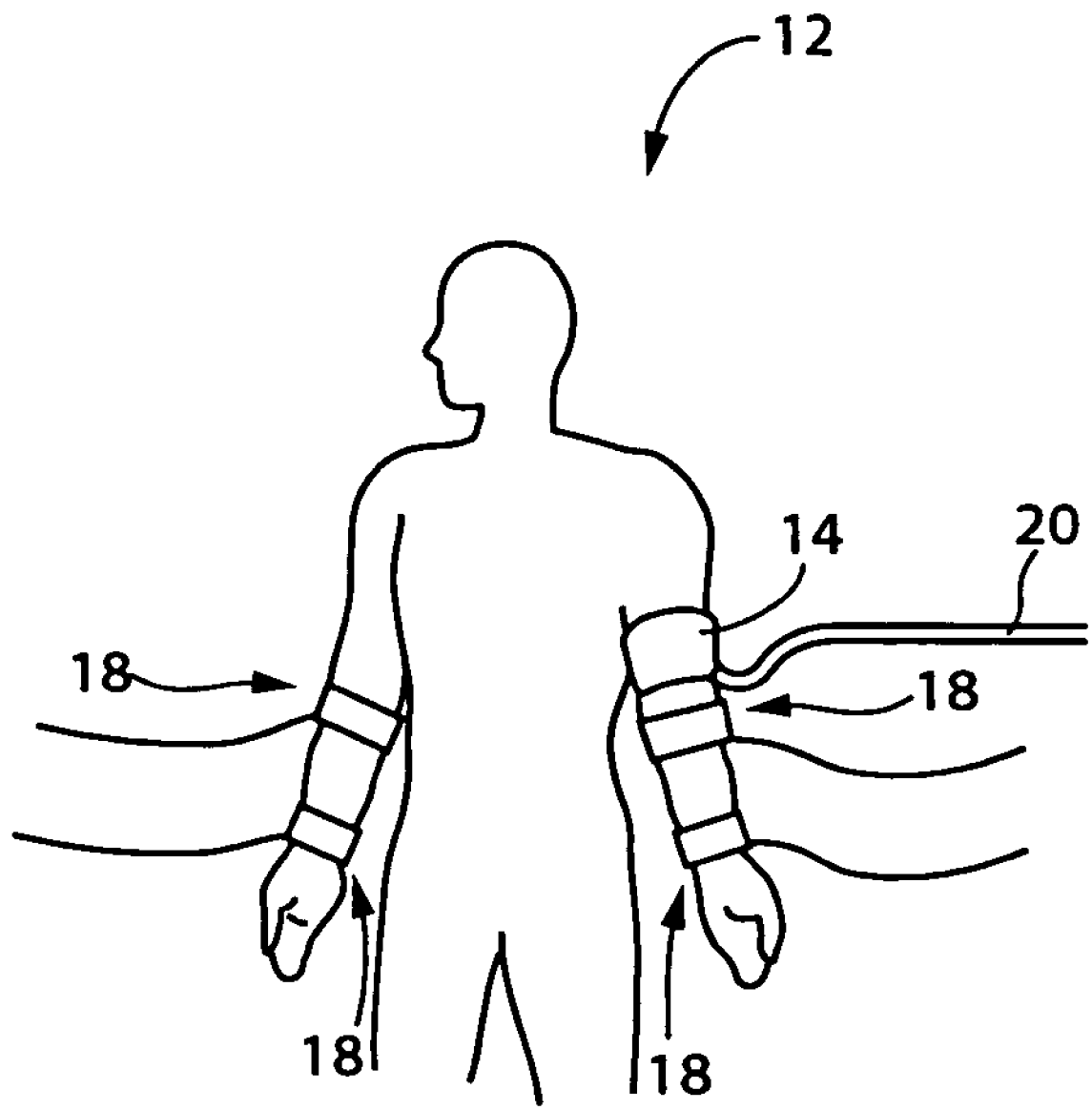
FIG. 15 is a view showing a state where the cuff and pressure pulse wave detecting probe provided in the vascular endothelial function assessment apparatus of the third embodiment are attached to the patient.

Next, an explanation will be made regarding the third embodiment of this invention. FIG. 15 is a view showing a state where the cuff 14 and pressure pulse wave detecting probe 18 provided in the vascular endothelial function assessment apparatus of the third embodiment are attached to the patient 12. As shown in FIG. 15, the third embodiment is provided with four pressure pulse wave detecting probes 18, which are attached to the right and left wrists, a site of the left upper arm downstream from the cuff 14 and a site of the right upper arm symmetrical to the site with respect to the median plane. In the third embodiment, the pulse-wave-conduction-velocity-relating information measurement apparatus 90 of the first embodiment to which the pressure pulse wave detecting probe 18 attached to the above right upper arm is structurally added is used as a pulse-wave-conduction-velocity-relating information measurement apparatus.

Figure 16:
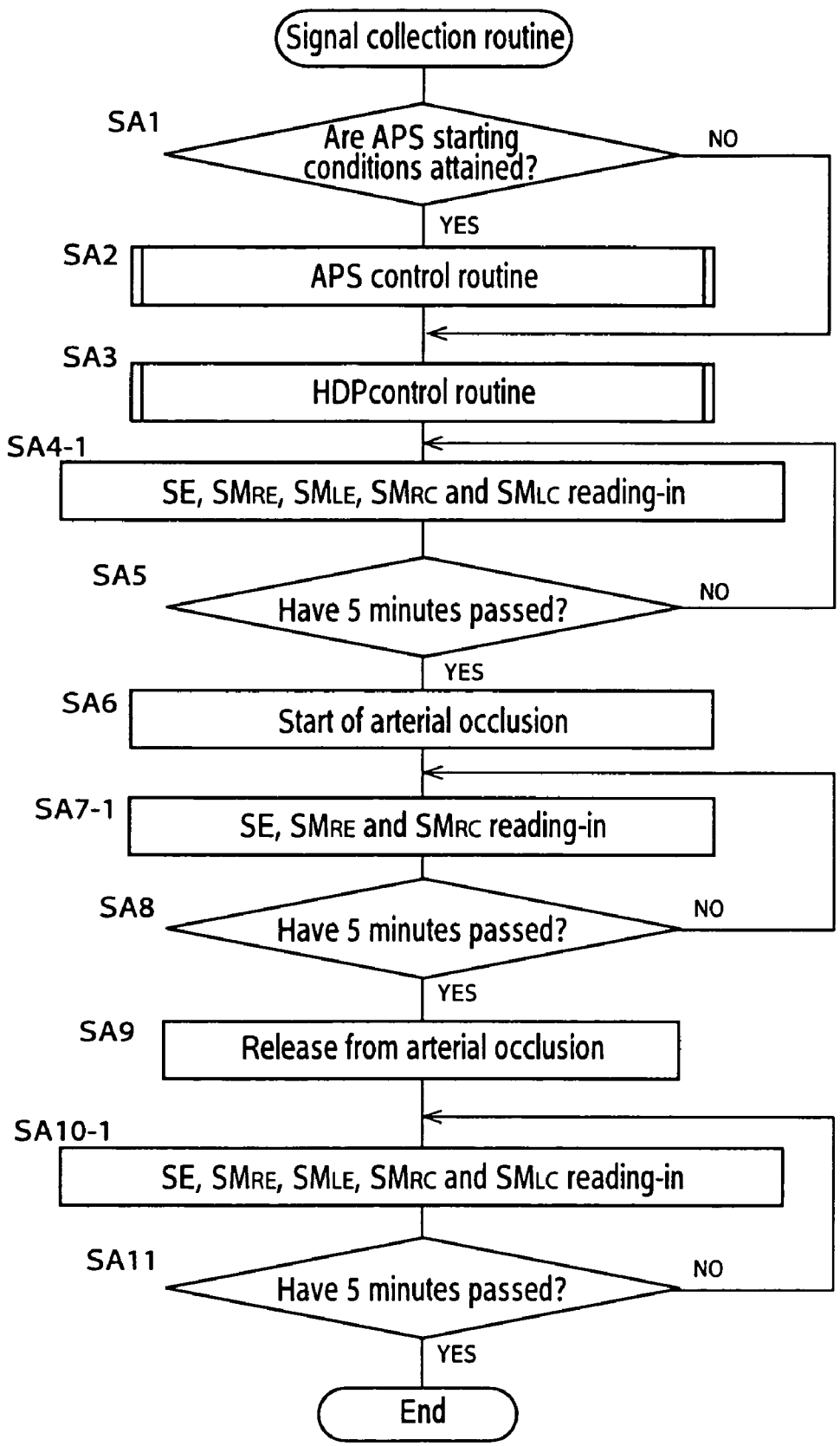
FIG. 16 is a flowchart describing major control operations of the electronic control device of the third embodiment, showing a signal collection routine.
Figure 17:
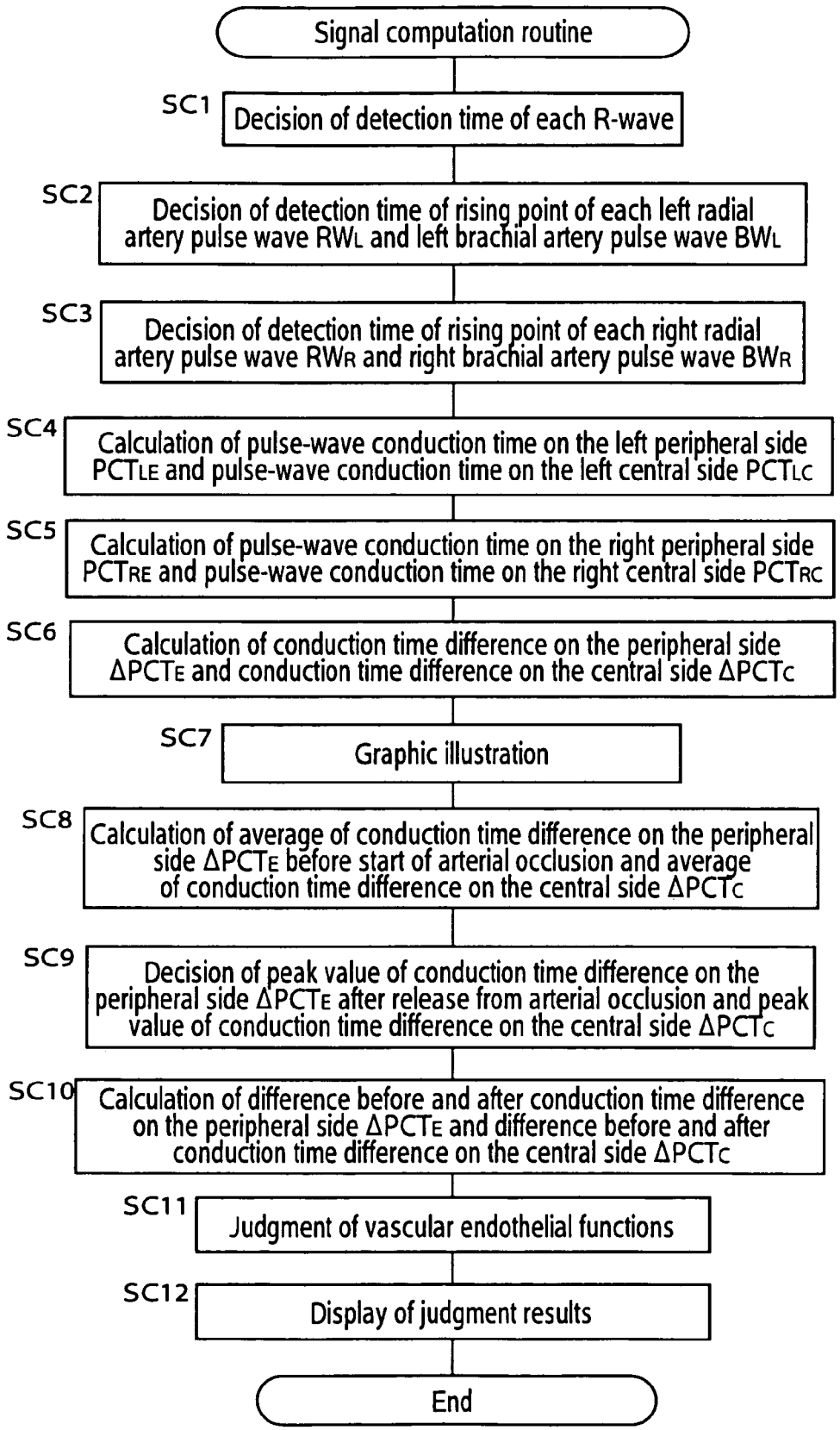
FIG. 17 is a flowchart describing major control operations of the electronic control device of the third embodiment, showing a signal computation routine.

The third embodiment is different from the first embodiment only in a larger number of pressure pulse wave detecting probes 18 by 2 and the control functions of the electronic control device 32. FIG. 16 and FIG. 17 are flowcharts showing major control operations of the electronic control device 32 of the third embodiment. FIG. 16 is a signal collection routine and FIG. 17 is a signal computation routine.

FIG. 16 is similar in content with FIG. 11 of the previously described first embodiment, except for an increased number of signals collected in steps SA4-1, SA7-1 and SA10-1. More particularly, in SA4-1 and SA10-1, a pressure pulse wave signal on the right central side $SM_{RC}$ which is a signal from the pressure pulse wave detecting probe 18 attached to the right upper arm closer to the central side than the right wrist and a pressure pulse wave signal on the left central side $SM_{LC}$ which is a signal from the pressure pulse wave detecting probe 18 attached to the left upper arm closer to the central side than the left wrist are read in, in addition to the electrocardiographic signal SE, a pulse wave signal on the right peripheral side $SM_{RE}$ which is a signal from the pressure pulse wave detecting probe 18 attached to the right wrist and a pressure pulse wave signal on the left peripheral side $SM_{LE}$ which is a signal from the pressure pulse wave detecting probe 18 attached to the left wrist. In SA7-1, the pulse wave signal on the right central side $SM_{RC}$ is read in, in addition to the electrocardiographic signal SE and the right pulse wave signal on the peripheral side $SM_{RE}$. Further, in FIG. 16, steps of SA4-1 through SA5 will function as a pre-stimulation measurement step in combination with steps SC1 through SC5 (FIG. 17) to be described later, and steps SA11-1 through SA11 will function as a post-stimulation measurement step in combination with the steps SC1 through SC5 (FIG. 17).

The computation routine of FIG. 17 will be carried out after completion of the signal collection routine of FIG. 16. An electrocardiogram represented by the electrocardiographic signal SE read in the steps SA4-1, SA7-1 and SA10-1 of FIG. 16 is referred to determine a detection point in time of R-wave for each pulse at first in SC1. Electrocardiograms represented by a pulse wave signal on the left peripheral side $SM_{LE}$ and a pulse wave signal on the left central side $SM_{LC}$ read in the steps SA4-1, SA7-1 and SA10-1 are referred to determine a rising point of the left radial artery pulse wave $RW_L$ and a rising point of the left brachial artery pulse wave $BW_L$ for each pulse. Then, in the subsequent SC3, electrocardiograms represented by a pulse wave signal on the right peripheral side $SM_{RE}$ and a pulse wave signal on the right central side $SM_{RC}$ read in the steps SA4-1, SA7-1 and SA10-1 are referred to determine a rising point of the right radial artery pulse wave $RW_R$ and a rising point of the right brachial artery pulse wave $BW_R$ for each pulse.

In the subsequent SC4, a difference between the time when a rising point of each left brachial artery pulse wave $BW_L$ determined in SC2 is detected and the time when a rising point of each left radial artery pulse wave $RW_L$ is detected is referred to make an over time calculation of the pulse-wave conduction time on the left peripheral side $PCT_{LE}$ in terms of a value for each pulse or an average of a few pulses. Further, a difference between the time when each R-wave of the electrocardiogram determined in SC1 is detected and the time when a rising point of each left brachial artery pulse wave $BW_L$ determined in SC2 is detected is referred to make an over time calculation of the pulse-wave conduction time on the left central side $PCT_{LC}$ in terms of a value for each pulse or an average of a few pulses. In the third embodiment of this invention, the above-mentioned pulse-wave conduction time on the left peripheral side $PCT_{LE}$ and the pulse-wave conduction time on the left central side $PCT_{LC}$ are equivalent respectively to the first pulse-wave-conduction-velocity-relating information and the third pulse-wave-conduction-velocity-relating information, and their measurement segments, namely, a segment from the left upper arm to the left wrist and a segment from the heart to the left upper arm are equivalent respectively to the first segment and the third segment.

Then, in SC5, a difference between the time when a rising point of each right brachial artery pulse wave $BW_R$ determined in SC2 is detected and the time when a rising point of each right radial artery pulse wave $RW_R$ is detected is referred to make an over time calculation of the pulse-wave conduction time on the right peripheral side $PCT_{RE}$ in terms of a value for each pulse or an average of a few pulses. Further, a difference between the time when each R-wave of the electrocardiogram determined in SC1 is detected and the time when a rising point of each right brachial artery pulse wave $BW_R$ determined in SC2 is detected is referred to make an over time calculation of the pulse-wave conduction time on the right central side $PCT_{RC}$ in terms of a value for each pulse or an average of a few pulses. In the third embodiment of this invention, the above-mentioned pulse-wave conduction time on the right peripheral side $PCT_{RE}$ and the pulse-wave conduction time on the right central side $PCT_{RC}$ are equivalent respectively to the second pulse-wave-conduction-velocity-relating information and the fourth pulse-wave-conduction-velocity-relating information, and their measurement segments, namely, a segment from the right upper arm to the right wrist and a segment from the heart to the right upper arm are equivalent respectively to the second segment and the fourth segment.

Then, in the subsequent SC6 equivalent to the comparative value calculating means and comparative value calculation step, the pulse-wave conduction time on the right peripheral side $PCT_{RE}$ calculated in SC5 is subtracted from the pulse-wave conduction time on the left peripheral side $PCT_{LE}$ calculated in SC4 to make an over time calculation of the conduction time difference on the peripheral side $\Delta PCT_E$ for 5 minutes before ischemia (namely, pre-ischemic comparative value on the peripheral side) and the conduction time difference on the peripheral side $\Delta PCT_E$ for 5 minutes after the release from ischemia (namely, post-ischemic comparative value on the peripheral side) in terms of a value for each pulse or an average of a few pulses. Further, the pulse-wave conduction time on the right central side $PCT_{RC}$ calculated in SC5 is subtracted from the pulse-wave conduction time on the left central side $PCT_{LC}$ calculated in SC4 to make an over time calculation of the conduction time difference on the central side $\Delta PCTc$ for 5 minutes before ischemia (namely, pre-ischemic comparative value on the central side) and the conduction time difference on the central side for 5 minutes after the release from ischemia $\Delta PCTc$ (namely, post-ischemic comparative value on the central side) in terms of a value for each pulse or an average of a few pulses.

In the subsequent SC7, changes over time in the pulse-wave conduction time on the left and right peripheral sides $PCT_{LE}$ and $PCT_{RE}$, pulse-wave conduction time on the left and right central sides $PCT_{LC}$, $PCT_{RC}$, conduction time difference on the peripheral side $\Delta PCT_E$ and conduction time difference on the central side $\Delta PCT_C$ calculated in the above-mentioned steps of SC4 through SC6 are given graphically on the display 74.

Then, steps of SC8 through SC12 equivalent to the vascular endothelial dysfunction judgment means and vascular endothelial dysfunction judgment step are carried out. In SC8, respectively averaged are the conduction time difference on the peripheral side $\Delta PCT_E$ and the conduction time difference on the central side $\Delta PCT_C$ for 3 minutes before start of ischemia, with regard to the conduction time difference on the peripheral side $\Delta PCT_E$ and the conduction time difference on the central side $\Delta PCT_C$ for 5 minutes before ischemia calculated in SC6.

Then, in the subsequent SC9, the respective determinations are made for the peak of the conduction time difference on the peripheral side $\Delta PCT_E$ after release from ischemia and the peak of the conduction time difference on the central side $\Delta PCT_C$ after release from ischemia calculated in SC6. Then, in SC10, the average of the conduction time difference on the peripheral side $\Delta PCT_E$ for 3 minutes before ischemia calculated in SC8 is subtracted from the peak of the conduction time difference on the peripheral side $\Delta PCT_E$ after the release from ischemia determined in SC9 to calculate a difference between the conduction time difference on the peripheral side $PCT_E$ before ischemia and that after ischemia. Further, the average of the conduction time difference on the central side $\Delta PCT_C$ for 3 minutes before ischemia calculated in SC8 is subtracted from the peak of the conduction time difference on the central side $\Delta PCT_C$ after release from ischemia determined in SC9 to calculate a difference between the conduction time difference on the central side $\Delta PCT_C$ before ischemia and that after ischemia.

Then, in the subsequent SC11, where a difference between the conduction time difference on the peripheral side $\Delta PCT_{TE}$ before ischemia and that after ischemia as calculated in the above SC10 is at or lower than a predetermined judgment standard value for the conduction time difference on the peripheral side $\Delta PCT_E$, it is judged that the vascular endothelial function in the segment from the left upper arm to the left wrist are impaired. Where the difference between the conduction time difference on the peripheral side $\Delta PCT_E$ before ischemia and that after ischemia is greater than the predetermined judgment standard value, it is judged that the vascular endothelial function in the segment from the left upper arm to the left wrist are normal. Further, where the difference between the conduction time difference on the central side $\Delta PCT_C$ before ischemia and that after ischemia calculated in the above SC10 is at or lower than the predetermined judgment standard value for the conduction time difference on the central side $\Delta PCT_C$, it is judged that the vascular endothelial function in the segment from the heart to the left upper arm are impaired. Where the difference between the conduction time difference on the central side $\Delta PCT_C$ before ischemia and that after ischemia is greater than the predetermined judgment standard value, it is judged that the vascular endothelial function from the heart to the left upper arm are normal. Then, in SC12, the message showing the results obtained in the above SC11 are displayed on the display 74.

According to the above third embodiment, in SC6 (comparative value calculating means and comparative value calculation step), the pulse-wave conduction time on the left peripheral side $PCT_{LE}$ at the first segment closer to the peripheral side than the left upper arm, which is a site of arterial occlusion, pulse-wave conduction time on the right peripheral side $PCT_{RE}$ at the second segment, which constitutes a pair with the first segment, are referred to calculate a conduction time difference on the peripheral side $\Delta PCT_E$ (comparative value) before and after ischemia closer to the peripheral side than the site of arterial occlusion. In addition, the pulse-wave conduction time on the left central side $PCT_{LC}$ and the pulse-wave conduction time on the right central side $PCT_{RC}$ before and after ischemia are respectively calculated at the third segment on the central side of the left brachial artery and at the fourth segment, which constitutes a pair with the third segment. In SC6 (comparative value calculating means and comparative value calculation step), the pulse-wave conduction time on the left central side $PCT_{LC}$ and pulse-wave conduction time on the right central side $PCT_{RC}$ are referred to calculate the conduction time difference on the central side $\Delta PCT_C$ (comparative value) before and after ischemia on the central side. Therefore, it is possible to separate the vascular endothelial function of the left brachial artery into those on the peripheral side and those on the central side and also make a simultaneous evaluation of them.

An explanation has been made in detail about the embodiments of this invention by referring to the drawings, however, other embodiments may be applied to the invention.

For example, in the above embodiments, a reactive hyperemia after transient ischemia is used to attain an increase in the arterial blood flow as a type of stimulation for inducing the release of endothelium-derived relaxing factors from vascular endothelium. A necessary hyperemic reaction can be obtained by warming or exercise of the hand. Thus, such warming or exercise may be used in place of arterial occlusion (ischemia) inducing reactive hyperemia. Further, in addition to inducing the release of endothelium-derived relaxing factors from vascular endothelium by the blood flow increasing response, administration of drugs such as acetylcholine is able to induce the release of endothelium-derived relaxing factors from vascular endothelium. Thus, these drugs may be administered in place of a type of stimulation for releasing endothelium-derived relaxing factors. Such administration methods include direct arterial injection, application of a drug on the skin at a specified region to be stimulated and systemic administration, for example, a method by which the blood flow into the above region can be blocked only for a period when blood concentrations of the drug are relatively high to prevent delivery of the drug into local areas for a certain period only.

Increased blood flow by reactive hyperemia is a type of stimulation for inducing the release of endothelium-derived relaxing factors. In contrast, stimulations may be given for inhibiting the release of endothelium-derived relaxing factors and for inhibiting the vascular dilation due to the release of endothelium-derived relaxing factors. When such stimulations are applied, since these stimulations are common to the previously-described embodiments in that a stimulus is given to change a diameter of the blood vessel, they can provide the same effect as obtained in the previously-described embodiments. These stimulations include administration of drugs, oxidation stress, inflammable cytokines (for example, interleukin 1, interleukin 6 and tumor necrosis factors) and hypoxia. In this instance, the oxidation stress takes place by smoking, mental stress, high levels of low-density lipoprotein and ischemic reperfusion. The drugs include nitrogen monoxide synthetase inhibitors which inhibit the release of nitrogen monoxide which is an endothelium-derived relaxing factor, a nitric acid agent which gives a prior saturation to vasodilation response due to endogenous endothelium-derived relaxing factors and nitrogen monoxide by itself. The drugs may be administered similarly as those inducing the release of the previously-described endothelium-derived relaxing factors.

In the previous embodiments, pulse-wave conduction time PCT is computed after all the signals are collected for measuring the pulse-wave conduction time PCT. The pulse-wave conduction time PCT may also be computed for each reading of a pulse or a few pulses.

In the previous embodiments, the pulse-wave conduction time PCT is calculated as pulse-wave-conduction-velocity-relating information. Pulse wave conduction velocity PWV may also be calculated in place of the pulse-wave conduction time PCT.

In the previous embodiments, the arterial occlusion apparatus 82 is used to carry out arterial occlusion at the upper arm. It may be also possible to carry out arterial occlusion at the forearm, wrist, femoral region, lower leg and ankle. Where arterial occlusion is carried out at these regions, arteries at occlusion sites (for example, the femoral artery) or arteries connecting with their upstream or downstream arteries undergo an increase in blood flow after the release from occlusion. Sites to be stimulated by increased blood flow are the arteries of occlusion sites and arteries connecting with their upstream or downstream arteries. Thus, in the first segment, the end of the upstream side includes, for example, the base of ascending aorta, cervical portion and upper arm, whereas the end of the downstream includes ankle and tips of the digits at the side where reactive hyperemia is carried out. Further, where arterial occlusion is carried out at the upper arm as explained in the previous embodiment, the first segment or the third segment is not restricted by the previous embodiments, and the end of the upstream in the first segment and the end of the downstream in the third segment may be the cervical portion, or the end of the downstream in the first segment may be the tips of the fingers.

In the previous embodiments, an electrocardiograph is used as a heartbeat-synchronous signal detection apparatus for detecting the electrocardiographic signal SE as a heartbeat-synchronous signal. A phonocardiographic microphone may be used as a heartbeat-synchronous signal detection apparatus for measuring a cardiac sound signal (phonocardiogram).

Further, in the previous first embodiment, the conduction time difference $\Delta PCT$ is calculated by subtracting the right pulse-wave conduction time $PCT_R$ from the left pulse-wave conduction time $PCT_L$. The conduction time difference $\Delta PCT$ may also be calculated by subtracting the left pulse-wave conduction time $PCT_L$ from the right pulse-wave conduction time $PCT_R$. Similarly, in the second embodiment, the conduction time ratio R (PCT) may be calculated by dividing the right pulse-wave conduction time $PCT_R$ by the left pulse-wave conduction time $PCT_L$.

In the previous embodiments, the conduction time difference $\Delta PCT$ before start of ischemia (or conduction time ratio R (PCT)) is subtracted from the peak of the conduction time difference $\Delta PCT$ after the release from ischemia (or conduction time ratio R (PCT)) to calculate the difference. It may be also possible that the peak of the conduction time difference $\Delta PCT$ after the release from ischemia (or conduction time ratio R (PCT)) is subtracted from the conduction time difference $\Delta PCT$ before start of ischemia (or conduction time ratio R (PCT)) to obtain the difference.

In the previous embodiments, the display 74 is used as an output apparatus. It may be also possible that the output apparatus is a printer.

It is further to be understood that various other changes may be made in the present invention, without departing from the spirit of the present invention.

What is claimed is:

1. An apparatus for assessing vascular endothelial function, comprising;
   an arterial occlusion apparatus for occluding arteries in a specified region in a living body for more than a predetermined time,
   a pulse-wave-conduction-velocity-relating information measurement apparatus for measuring successively a first pulse-wave-conduction-velocity-relating information which is a pulse-wave-conduction-velocity-relating information related to the velocity at which a pulse conducts through the artery in a first segment including a part or a whole of the specified region of said artery and the second pulse-wave-conduction-velocity-relating information which is a pulse-wave-conduction-velocity-relating information of the artery in a second segment almost symmetric to said first segment with respect to the median plane, and
   comparative value calculating means for calculating a pre-ischemic comparative value representing a difference or ratio of said first pulse-wave-conduction-velocity-relating information to said second pulse-wave-conduction-velocity-relating information before ischemia by said arterial occlusion apparatus and also for calculating a post-ischemic comparative value representing a difference or ratio of said first pulse-wave-conduction-velocity-relating information to said second pulse-wave-conduction-velocity-relating information after release from ischemia (arterial occlusion) by said arterial occlusion apparatus.

2. The apparatus for assessing vascular endothelial function according to claim 1 wherein said first segment is a segment from the heart to a specified point on said artery and said second segment is a segment almost symmetric to a segment from the heart to a specified point on said artery with respect to the median plane.

3. The apparatus for assessing vascular endothelial function according to claim 1, wherein
   said comparative value calculating means is for calculating successively said post-ischemic comparative value, and further comprising
   a vascular endothelial dysfunction judgment means for judging an impairment of vascular endothelial function on the basis of the fact that an absolute value of a difference between a peak value of the post-ischemic comparative value and the pre-ischemic comparative value calculated successively by the comparative value calculating means is at or lower than a predetermined judgment standard value.

4. The apparatus for assessing vascular endothelial function according to claim 1, wherein
   said comparative value calculating means is for calculating successively said post-ischemic comparative value, and further comprising an output apparatus for illustrating graphically changes over time in comparative values calculated successively by said comparative value calculating means.

5. The apparatus for assessing vascular endothelial function according to claim 1, wherein said first segment is closer to the peripheral side than a region of arterial occlusion by said arterial occlusion apparatus, said pulse-wave-conduction-velocity-relating information measurement apparatus is for measuring almost simultaneously a third pulse-wave-conduction-velocity-relating information which is said pulse-wave-conduction-velocity-relating information at a specified third segment closer to the central side rather than said arterial occlusion region and a fourth pulse-wave-conduction-velocity-relating information which is said pulse-wave-conduction-velocity-relating information at a fourth segment almost symmetric to said third segment with respect to the median plane, in addition to said first pulse-wave-conduction-velocity-relating information and the second pulse-wave-conduction-velocity-relating information, and said comparative value calculating means is for calculating respectively a pre-ischemic comparative value on the central side representing a difference or ratio of said third pulse-wave-conduction-velocity-relating information to said fourth pulse-wave-conduction-velocity-relating information obtained before ischemia by said arterial occlusion apparatus, and a post-ischemic comparative value on the central side representing a difference or ratio of the third pulse-wave-conduction-velocity-relating information to the fourth pulse-wave-conduction-velocity-relating information obtained after release from ischemia (arterial occlusion) by said arterial occlusion apparatus, in addition to the pre-ischemic comparative value on the peripheral side representing a difference or ratio of said first pulse-wave-conduction-velocity-relating information to the second pulse-wave-conduction-velocity-relating information obtained before ischemia by said arterial occlusion apparatus and post-ischemic comparative value on the peripheral side representing a difference or ratio of said first pulse-wave-conduction-velocity-relating information to said second pulse-wave-conduction-velocity-relating information obtained after release from ischemia (arterial occlusion) by said arterial occlusion apparatus.

* * * * *